(12) United States Patent
Iwase

(10) Patent No.: US 9,307,902 B2
(45) Date of Patent: Apr. 12, 2016

(54) IMAGE PROCESSING DEVICE, IMAGE PROCESSING SYSTEM, IMAGE PROCESSING METHOD, AND PROGRAM

(71) Applicant: CANON KABUSHIKI KAISHA, Tokyo (JP)

(72) Inventor: Yoshihiko Iwase, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 89 days.

(21) Appl. No.: 14/209,549

(22) Filed: Mar. 13, 2014

(65) Prior Publication Data

US 2014/0268048 A1  Sep. 18, 2014

(30) Foreign Application Priority Data

Mar. 15, 2013 (JP) ................................. 2013-053599

(51) Int. Cl.
*A61B 3/14* (2006.01)
*A61B 3/10* (2006.01)

(52) U.S. Cl.
CPC ...................................... *A61B 3/102* (2013.01)

(58) Field of Classification Search
USPC .................................................. 351/200–246
See application file for complete search history.

(56) References Cited

U.S. PATENT DOCUMENTS

| 2010/0007848 | A1  | 1/2010  | Murata |
|---|---|---|---|
| 2012/0281235 | A1  | 11/2012 | Murata |
| 2014/0028875 | A1* | 1/2014  | Hara ........................... 348/231.5 |
| 2014/0086488 | A1* | 3/2014  | Moteki et al. ................. 382/182 |

FOREIGN PATENT DOCUMENTS

| CN | 101023861 A   | 8/2007 |
|---|---|---|
| EP | 2141446 A1    | 1/2010 |
| JP | 2011-217811 A | 11/2011 |
| JP | 2012-161595 A | 8/2012 |

\* cited by examiner

*Primary Examiner* — Mohammed Hasan
(74) *Attorney, Agent, or Firm* — Canon U.S.A. Inc., IP Division

(57) ABSTRACT

A new tomographic image is generated using a reverse image in which at least one portion of a tomographic image of a retina of an eye to be examined is reversed and the tomographic image so that the reverse image is located on a side on which the retinal layer in the tomographic image is in contact with an end of the tomographic image.

29 Claims, 14 Drawing Sheets

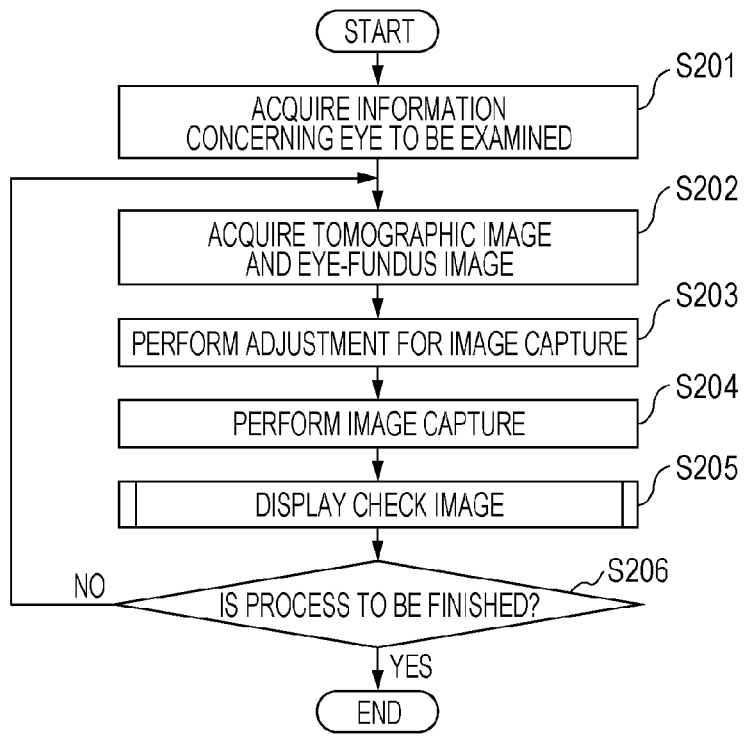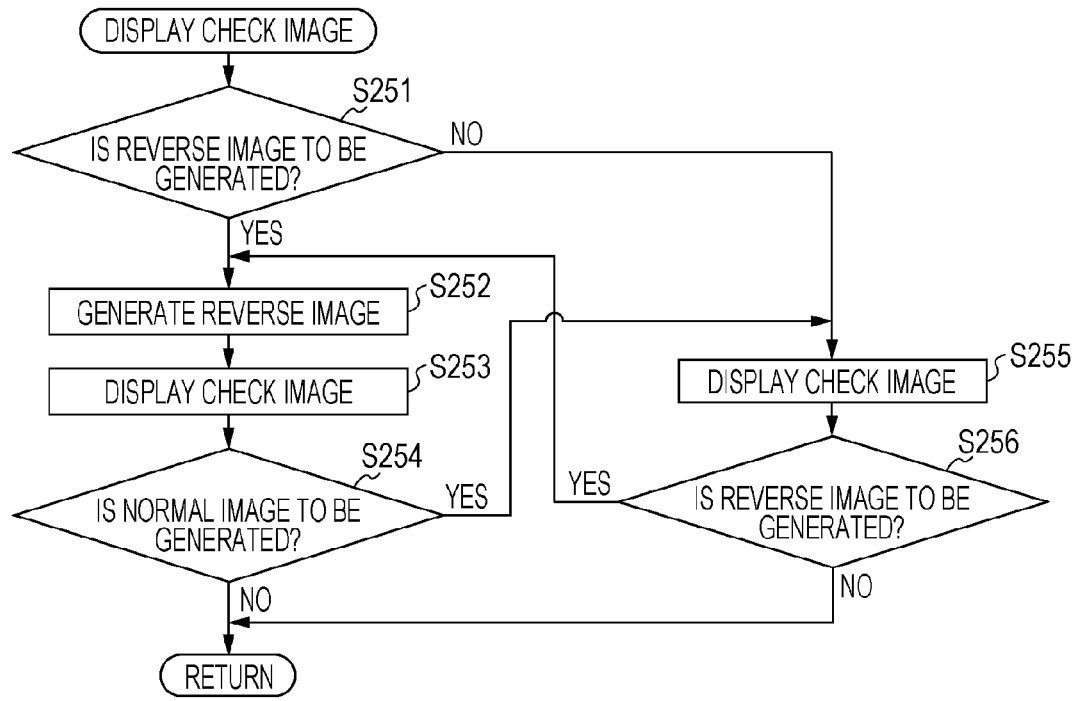

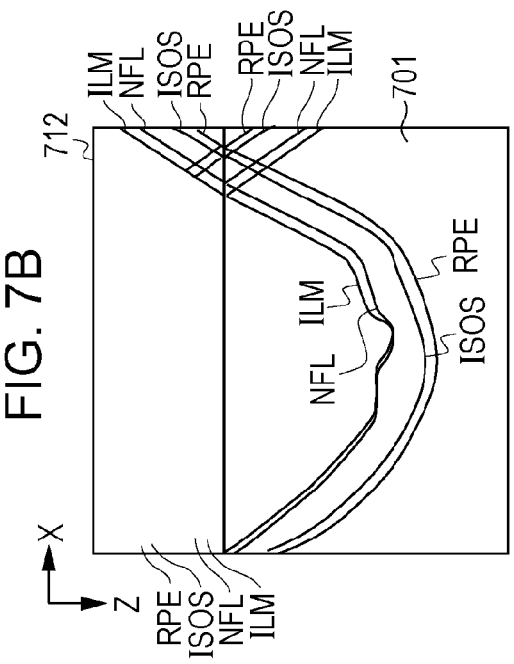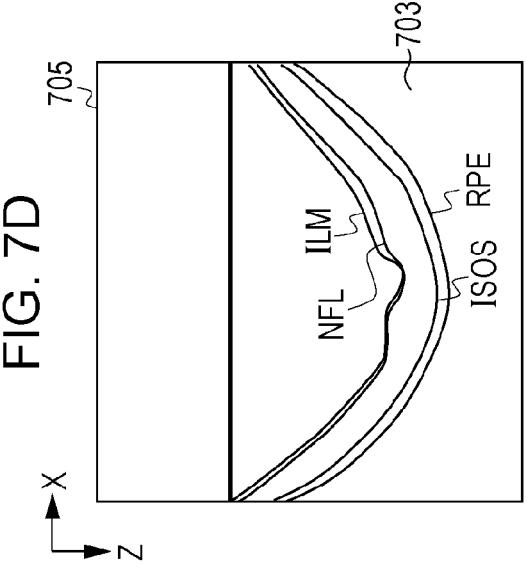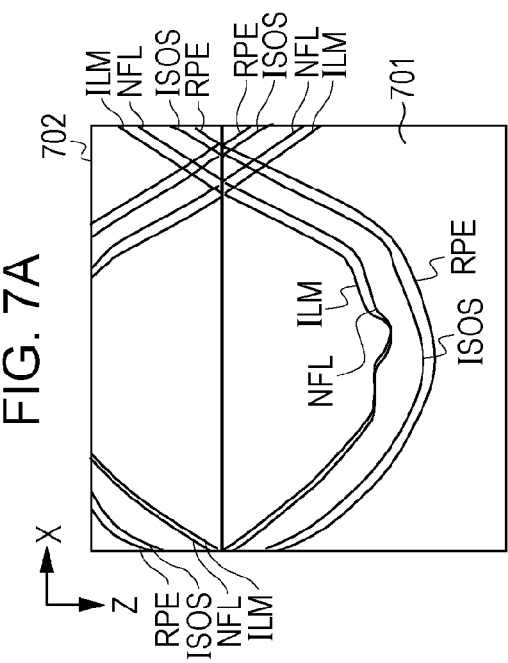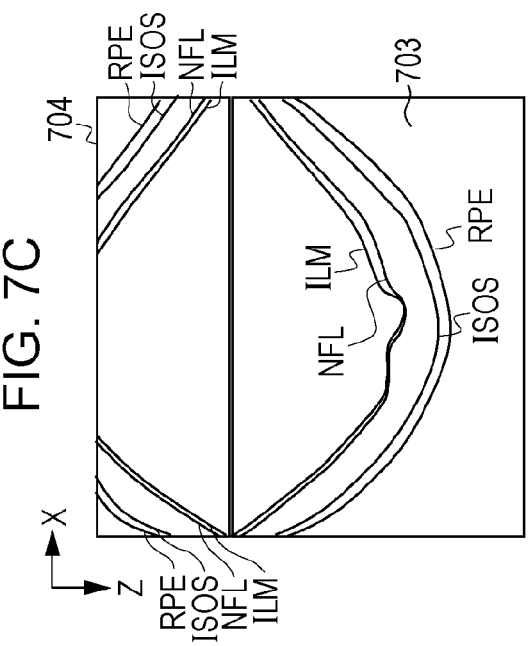

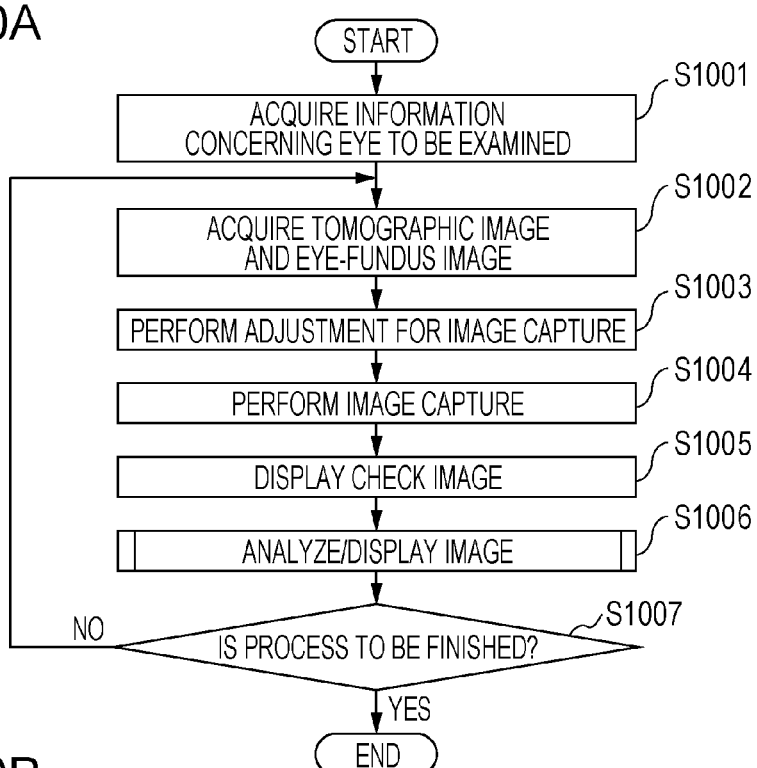
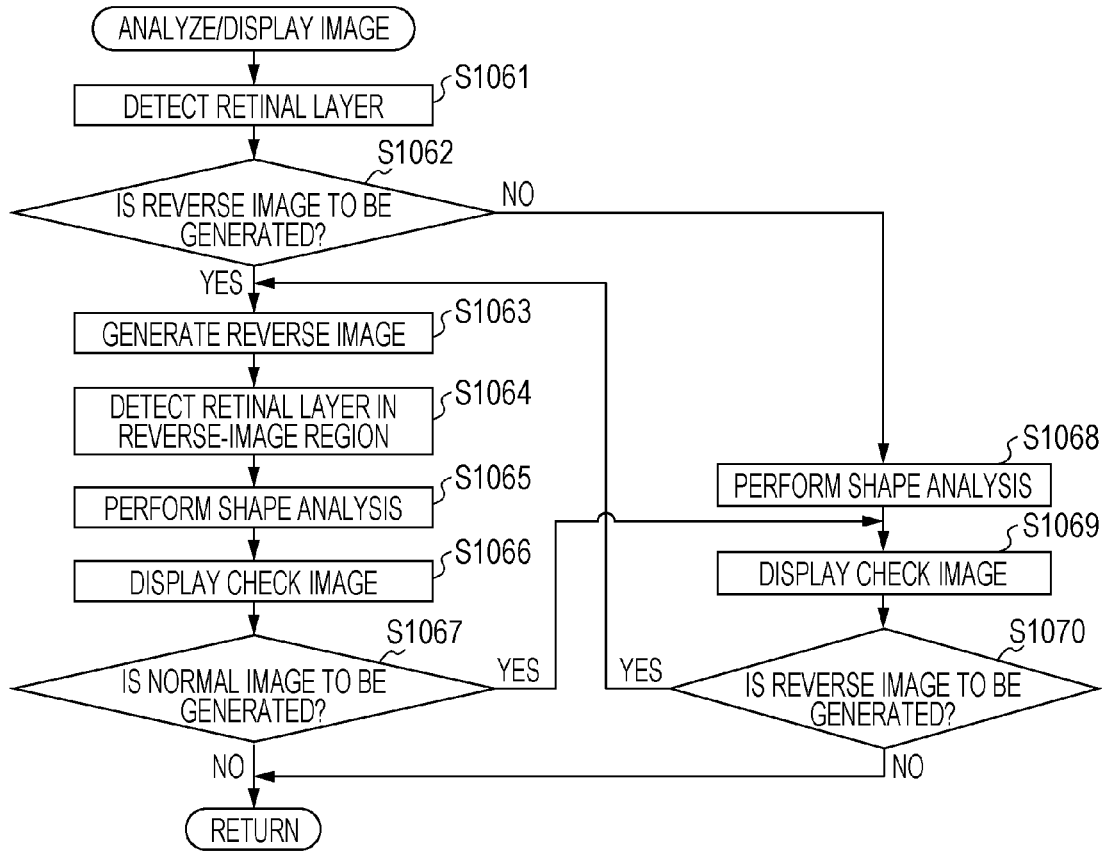

IMAGE PROCESSING DEVICE, IMAGE PROCESSING SYSTEM, IMAGE PROCESSING METHOD, AND PROGRAM

BACKGROUND OF THE INVENTION

1. Field of the Invention

The present invention relates to an image processing device, an image processing system, an image processing method, and a program, and, more particularly, relates to an image processing device, an image processing system, an image processing method, and a program that use a tomographic image of an eye portion.

2. Description of the Related Art

Tomographic-image capturing devices for an eye portion, such as optical coherence tomography (OCT) devices, can three-dimensionally observe the state of the inside of the retinal layer. Because such a tomographic-image capturing device is useful in more accurately diagnosing a disease, the tomographic-image capturing device has attracted attention in recent years. As a type of OCT, for example, there is time domain OCT (TD-OCT) in which a supercontinuum light source and a Michelson interferometer are used in combination. This is configured to obtain information concerning depth resolution in such a manner that interference light which interferes with back-scattered light for a signal arm is measured by scanning the delay of a reference arm. However, with such TD-OCT, acquisition of an image at a high speed is difficult. Thus, as a method for acquiring an image at a higher speed, spectral domain OCT (SD-OCT) is known as OCT in which a supercontinuum light source is used and in which an interferogram is acquired by a spectrometer. Furthermore, swept source OCT (SS-OCT) is known, in which a method for measuring a spectrum interference with a single-channel photodetector is used by using a high-speed wavelength-sweeping light source as a light source.

If a morphological change of the retina can be measured in a tomographic image captured using any one of the above-mentioned OCTs, quantitative diagnosis can be performed for the progress of a disease such as glaucoma or the degree of recovery after treatment. In order to quantitatively measure a morphological change of the retina, a technique in which, using a computer, the boundaries between individual layers of the retina are detected from a tomographic image and in which the thicknesses of the layers are measured is disclosed in Japanese Patent Laid-Open No. 2011-217811.

SUMMARY OF THE INVENTION

An image processing device according to the present invention includes an acquisition unit configured to acquire a tomographic image of a retina of an eye to be examined; and a generating unit configured to generate a new tomographic image, using a reverse image in which at least one portion of the acquired tomographic image is reversed and the acquired tomographic image, so that the reverse image is located on a side on which a retinal layer in the acquired tomographic image is in contact with an end of the acquired tomographic image.

Further features of the present invention will become apparent from the following description of exemplary embodiments with reference to the attached drawings.

BRIEF DESCRIPTION OF THE DRAWINGS

FIGS. 2A and 2B are flowcharts illustrating the flow of a process performed in an image processing device according to the first embodiment.

FIGS. 7A to 7D are diagrams for explaining generation of a reverse image which is performed in an image processing device according to the second embodiment.

FIGS. 10A and 10B are flowcharts illustrating the flow of a process performed in an image processing device according to the third embodiment.

DESCRIPTION OF THE EMBODIMENTS

First Embodiment

Generate New Tomographic Image Using Reverse Image of Tomographic Image

Hereinafter, a first embodiment of the present invention will be described with reference to the drawings. Note that, in an image processing system including an image processing device according to the present embodiment, even when a tomographic image of the retinal layer that is highly curved, such as the retinal layer of a highly myopic eye, has been captured, display is performed so that the shape of the entire retinal layer can be grasped.

Here, when the retina is highly curved, such as the retina of a highly myopic eye, the retina layer is folded back in the upper portion of a tomographic image. Thus, there are cases in which image capture or analysis is not correctly performed.

Figure 14:
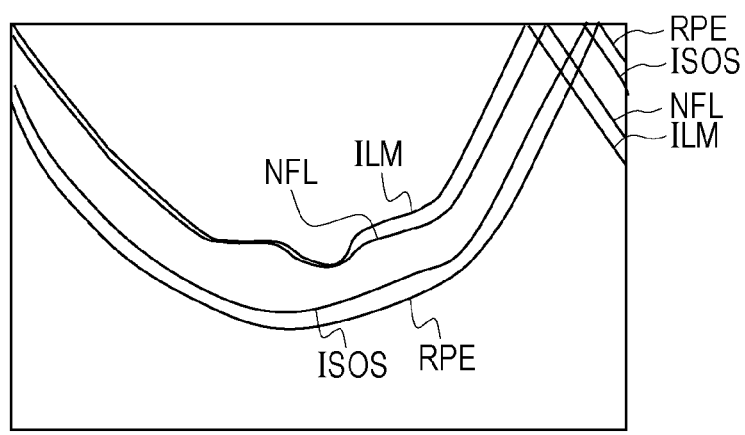
FIG. 14 is a diagram for explaining folding back of the retinal layer in the upper end portion of a tomographic image.

For example, the case where a coherence gate position is specified on the vitreous-humor side and where a tomographic image of an eye in which the retinal layer is highly curved is captured will be described using FIG. 14. As illustrated in FIG. 14, when the retinal layer is highly curved, there is a case in which a tomographic image is captured so that the retinal layer is in contact with the upper end portion of the tomographic image. In a portion of a tomographic image on the right side thereof illustrated in FIG. 14, an image in which the portion is folded back is generated. Accordingly, in such a portion, because the retinal layer is folded back and superimposed on itself, it is difficult to easily grasp the shape of the retinal layer.

The present embodiment has been made in view of the foregoing problem, and aims to easily observe the shape of the retinal layer even when a tomographic image has been captured so that the retinal layer is in contact with an end of the tomographic image.

For this reason, a new tomographic image is generated, using a reverse image in which at least one portion of a tomographic image of the retina of an eye to be examined is reversed and the tomographic image, so that the reverse image is located on a side on which the retinal layer in the tomographic image is in contact with an end of the tomographic image.

Accordingly, even when a tomographic image has been captured so that the retinal layer is in contact with an end of the tomographic image, the shape of the retinal layer can be easily observed.

Hereinafter, an image processing system including an image processing device according to the present embodiment will be described in detail.

Figure 1:
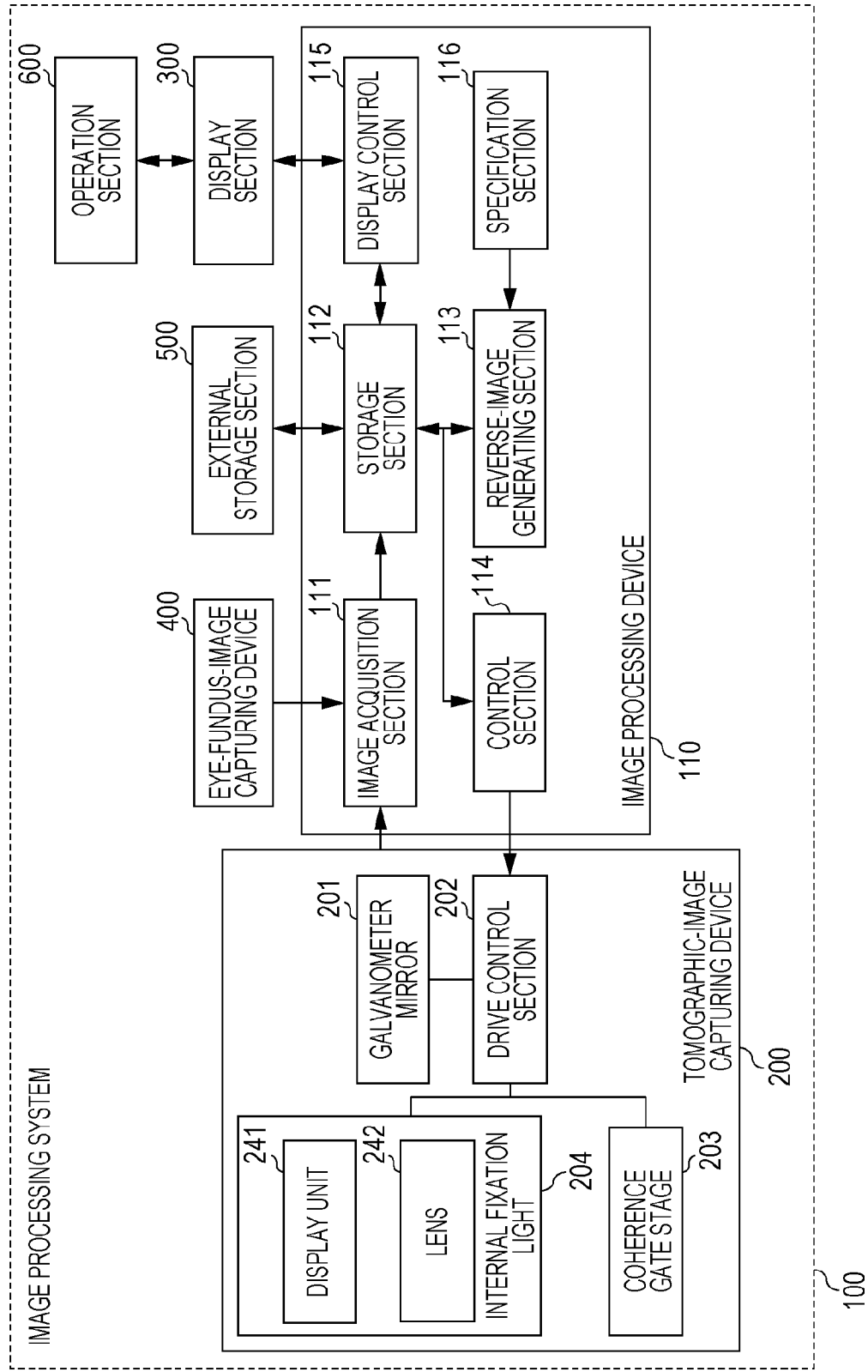
FIG. 1 is a diagram illustrating a configuration of an image processing system according to a first embodiment.

FIG. 1 is a diagram illustrating a configuration of an image processing system 100 including an image processing device 110 according to the present embodiment. As illustrated in FIG. 1, the image processing system 100 is configured so that the image processing device 110 is connected via an interface to a tomographic-image capturing device 200 (OCT device), a display section 300, an eye-fundus-image capturing device 400, an external storage section 500, and an operation section 600 so as to be capable of communicating with them in a wired or wireless manner.

The tomographic-image capturing device 200 is a device that captures a tomographic-image of an eye portion. A device used as the tomographic-image capturing device is configured using, for example, SD-OCT or SS-OCT. Note that, because the tomographic-image capturing device 200 is a known device, a detailed description thereof is omitted. Here, an image capture range for a tomographic image and an internal fixation light 204 will be described.

Referring to FIG. 1, a galvanometer mirror 201 is used to scan, using measurement light, the fundus of an eye, and defines the image capture range in which an image of the fundus of the eye is to be captured using OCT. Furthermore, a drive control section 202 controls the drive range and the speed of the galvanometer mirror 201, thereby defining the image capture range in the plain direction of the fundus of the eye and the number of scan lines (a scanning speed in the plain direction). Here, the galvanometer mirror includes two mirrors that are an X-scanning mirror and a Y-scanning mirror, and can scan, using the measurement light, a desired range of the fundus of the eye.

The internal fixation light 204 includes a display unit 241, and a lens 242. As the display unit 241, a unit in which a plurality of light emitting diodes (LDs) are disposed in a matrix is used. The lighting position of the light emitting diodes is changed by control of the drive control section 202 in accordance with a portion whose image is desired to be captured. Light emitted from the display unit 241 is led via the lens 242 to an eye to be examined. The light emitted from the display unit 241 has a wavelength of 520 nm, and a desired pattern is displayed by the drive control section 202.

A coherence gate stage 203 is controlled by the drive control section 202 in order to deal with, for example, the differences among the eye axial lengths of eyes to be examined. A coherence gate indicates a position at which the optical path length of the measurement light and the optical path length of reference light are equal to each other in OCT.

The eye-fundus-image capturing device 400 is a device that captures an image of the fundus of the eye of an eye portion. Examples of the device include a fundus camera, and a scanning laser ophthalmoscope (SLO).

The image processing device 110 includes an image acquisition section 111, a storage section 112, a reverse-image generating section 113, a control section 114, a display control section 115, and a specification section 116. The image acquisition section 111 acquires a tomographic image captured by the tomographic-image capturing device 200 and an eye-fundus image captured by the eye-fundus-image capturing device 400, and stores the tomographic image and the eye-fundus image in the storage section 112. The reverse-image generating section 113 generates a reverse image in which at least one portion of the tomographic image is reversed. The specification section 116 provides, for the reverse-image generating section 113, a specification for performing generation of a reverse image. Note that the reverse-image generating section 113 also functions as a generating section configured to generate, using a reverse image and a tomographic image, a new tomographic image so that the reverse image is located on a side on which the retinal layer in the tomographic image is in contact with an end of the tomographic image. Furthermore, the control section 114 performs control for the tomographic-image capturing device 200 so that the tomographic-image capturing device 200 will be controlled using image capture parameters which are set. Moreover, the external storage section 500 holds information concerning an eye to be examined (the name, age, gender, and so forth of a patient), captured image data, image capture parameters, image analysis parameters, and a parameter specified by an operator so that the information is associated with each of them. Additionally, the operation section 600 is, for example, a mouse, a keyboard, or a touch operation screen. The operator provides an instruction or an input, via the operation section 600, for the image processing device 110, the tomographic-image capturing device 200, or the eye-fundus-image capturing device 400.

Figure 3:
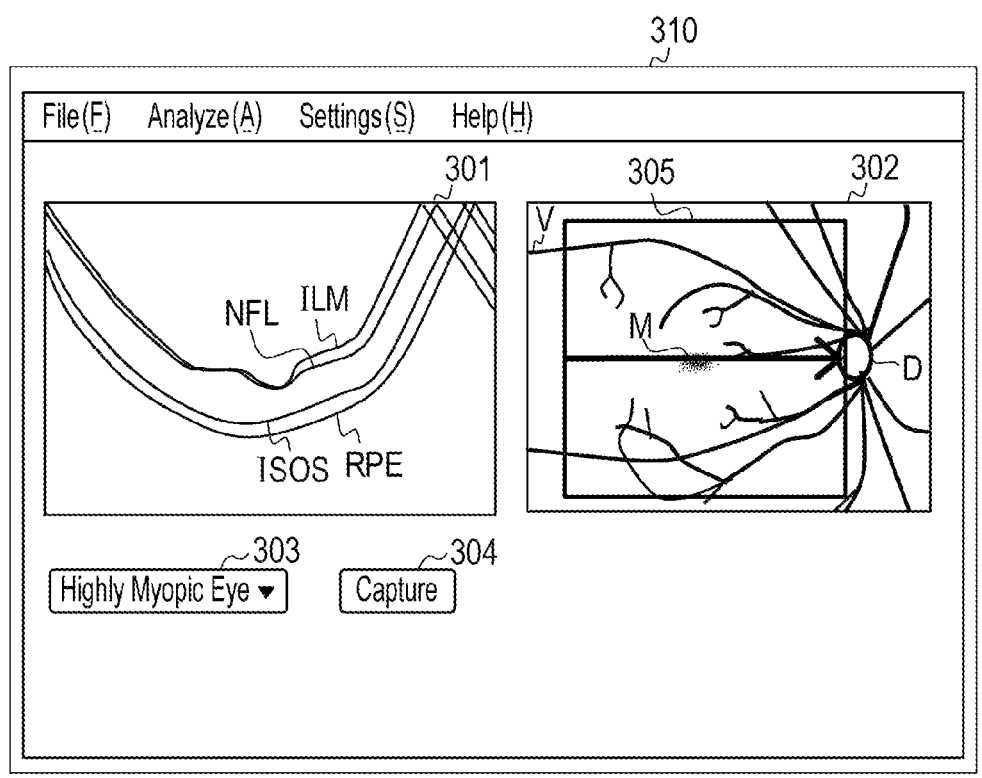
FIG. 3 illustrates an example of display, in the case of image capture, in a display screen of a display section of the image processing system according to the first embodiment.

Next, the procedure of a process of the image processing device 110 according to the present embodiment will be described with reference to FIGS. 2A and 2B and FIG. 3. FIGS. 2A and 2A are flowcharts illustrating the flow of a process of the operation of the entire present system according to the present embodiment. FIG. 3 illustrates an example of a display screen displayed on the display section 300 in the case of image capture in the present embodiment. In FIG. 3, reference numeral 310 denotes a tomographic-image capture screen. Reference numeral 301 denotes a tomographic image. Reference numeral 302 denotes an eye-fundus image. Reference numeral 303 denotes a combo box for selecting an image capture mode. Reference numeral 304 denotes an image-capture instruction button. Reference numeral 305 denotes a mark representing the image capture region, and is superimposed and displayed on the eye-fundus image 302. M represents a macular area, D represents an optic disc area, and V represents blood vessels.

Step S201

In step S201, an eye-to-be-examined information acquisition section that is not illustrated acquires, from the outside, a subject-person identification number as information by which an eye to be examined is identified. The eye-to-be-examined information acquisition section acquires, on the basis of the subject-person identification number, information concerning the eye to be examined that is information held by the external storage section 500, and stores the information in the storage section 112.

Step S202

In step S202, as pre-scan images used to check an image capture position in the case of image capture, the image acquisition section 111 acquires an eye-fundus image from the eye-fundus-image capturing device 400, and acquires a tomographic image from the tomographic-image capturing device 200.

Step S203

In step S203, various types of adjustment processes are performed in order to perform image capture. More specifically, at least the position of the internal fixation light, a scan range, a scan pattern, and the coherence gate position are set. The drive control section 202 controls the light emitting diodes of the display unit 241, thereby controlling the position of the internal fixation light 204 so that an image of the center of the macular area or the optic disc area will be captured.

Regarding the scan range, for example, a range of 9 to 15 mm is set as the image capture range of the tomographic-image capturing device 200. However, the values mentioned here are examples, and may be changed in accordance with the specifications of the device. The scan pattern is any one of various types of scan patterns for scans such as a raster scan, a cross scan, and a radial scan. Image capture is performed using the scan pattern specified by the operator. The process will be described supposing that image capture with the coherence gate whose position is located on the vitreous-humor side will be performed.

Furthermore, an image capture mode in the case of image capture is selected. Here, the process will be described supposing that selection of an image capture mode will be performed using the combo box 303 for selecting an image capture mode. It is supposed that an image capture mode for a highly myopic eye or an image capture mode for an eye that is not highly myopic can be selected using the combo box 303 for image capture modes. In the present embodiment, the case where image capture will be performed in the image capture mode for a highly myopic eye will be described. Note that it is supposed that image capture modes are set in advance using a plurality of combinations of a scan pattern and the position of an image-capture fixation light, and that image capture modes which are frequently utilized are set. Examples of the image capture modes frequently utilized include an image capture mode for glaucoma. In the case of image capture, the image capture mode for a highly myopic eye is selected, whereby the specification section 116 provides, for the reverse-image generating section 113, a specification for generating a reverse image.

Step S204

In step S204, capture of an image of the eye to be examined is performed. For example, when the operator selects the image-capture instruction button 304 in the tomographic-image capturing screen 310, the tomographic-image capturing device 200 controls the drive control section 202 to cause the galvanometer mirror 201 to operate, thereby capturing a tomographic image. The galvanometer mirror 201 includes an X scanner for the horizontal direction and a Y scanner for the vertical direction. Thus, when the orientation of each of the scanners is changed, a scan in a corresponding one of the horizontal direction (X) and the vertical direction in a coordinate system of the tomographic-image capturing device 200 can be performed. Because the orientations of the scanners are changed simultaneously, a scan in a direction obtained by combining the horizontal direction and the vertical direction can be performed. Thus, a scan in any direction in a plane of the fundus of the eye can be performed.

Step S205

Figure 4A:
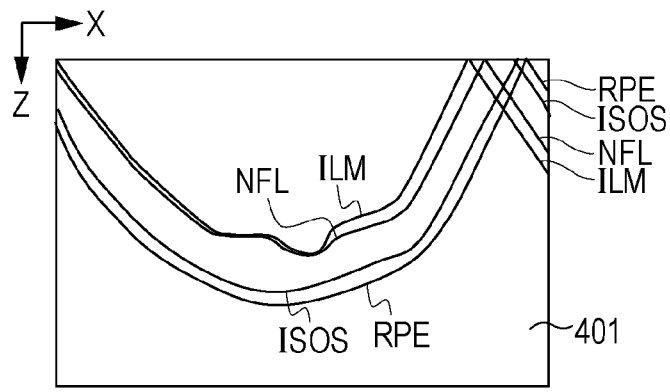
FIGS. 4A to 4C are diagrams for explaining generation of a reverse image which is performed in the image processing device according to the first embodiment.

In step S205, the tomographic image that has been captured in step S204 is displayed. This process will be described with reference to FIG. 2B and FIG. 4.

Step S251

In step S251, whether or not a specification for generating a reverse image has been provided in the case of image capture in step S204 is determined. In the present embodiment, supposing that a specification for generating a reverse image has been provided by selecting the image capture mode for a highly myopic eye, the process proceeds to step S252. Note that, in the case where the image capture mode for a highly myopic eye is not selected in the case of image capture, the process proceeds to step S255. Note that step S255 will be described below. Here, in the present embodiment, in the case where the image capture mode for a highly myopic eye is selected before image capture is performed, a reverse image is generated after the image capture has been performed. However, a configuration in which whether or not a reverse image is to be generated is selected after the image capture has been performed may be used. For example, when a display form which is displayed on a monitor and which indicates generation or display of a reverse image accepts an instruction provided by an operation of the operation section 600 that is an operation performed by the operator, generation or display of a reverse image may be performed.

Step S252

Figure 4B:
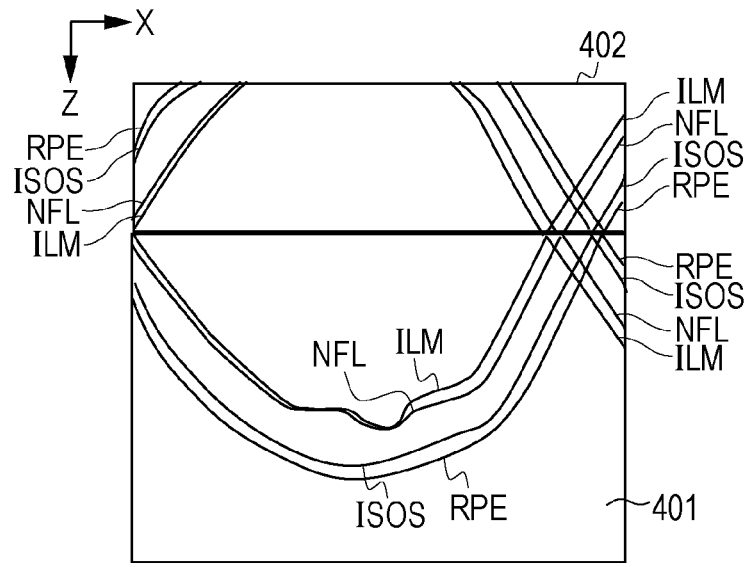
Figure 4C:
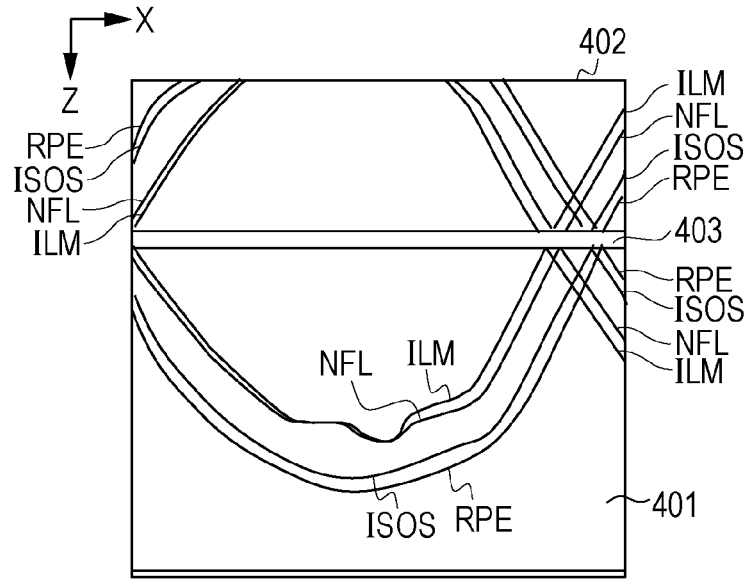

In step S252, generation of a reverse image is performed. This will be described using FIGS. 4A to 4C. Reference numeral 401 illustrated in FIG. 4A denotes an example of a captured tomographic image of a highly myopic eye. As shown as the tomographic image 401, a tomographic image in which one portion of the retinal layer is folded back because the retinal layer is highly curved is captured. Here, the reverse-image generating section 113 generates a reverse image having a certain range, which is decided in advance, so that such a folded-back portion of the retinal layer will be corrected. This will be described using FIG. 4B. FIG. 4B illustrates the tomographic image 401 and a reverse image 402. The reverse image 402 is an image obtained by copying a tomographic image in a certain range from the upper end portion of the tomographic image 401 in the depth direction (in the Z direction) and by reversing the copied tomographic image upside down. In this manner, a tomographic image can be generated so that the folded-back portion will be corrected. Note that the size of the region of the tomographic image in the depth direction which is a region to be copied may be decided on the basis of a value which is input in advance. Alternatively, an input section that is not illustrated may be displayed, and the operator may input a value to decide the size of the region. Furthermore, supposing that the range of the tomographic image 401 in the depth direction is about 1000 pixels (which corresponds to 2.0 mm), the range of the reverse image 402 in the depth direction can be, for example, larger than 200 pixels. Accordingly, even when the retinal layer of a highly myopic eye is folded back, the folded-back portion is displayed as a reverse image. In FIG. 4B, the tomographic image 401 and the reverse image 402 are in contact with each other, thereby providing one tomographic image. Here, as the case where the tomographic image 401 is generated by performing image reconstruction from sensor signals, there is a case where the tomographic image 401 is generated by removing a noise region corresponding to an autocorrelation function in the upper portion of the tomographic image 401. In this case, the tomographic image 401 and the reverse image 402 can be generated with consideration of the size of the removed noise region. An example in which the size of the removed noise region is taken into consideration is illustrated in FIG. 4C. In FIG. 4C, reference numeral 403 denotes an adjustment region corresponding to the noise region that is removed when the tomographic image 401 is generated and that corresponds to the autocorrelation function. The size of the adjustment region 403 in the horizontal direction is equal to the number of lines for an A scan. Regarding the size of the adjustment region 403 in the depth direction, supposing that the size of the noise region which is cut out when the tomographic image is generated is d, the size of the adjustment region 403 in the depth direction is 2d with consideration of a reverse portion. The pixel value of the adjustment region 403 can be a value close to a pixel value of a background region. Thus, an average value of pixel values of the background region from which the retinal layer is excluded may be obtained, and may be used as the pixel value of the adjustment region 403. Alternatively, a value (for example, 0) that is decided in advance may be used. In this manner, FIG. 4C illustrates one tomographic image constituted by the tomographic image 401, the reverse image 402, and the adjustment region 403. Note that the range of 2d that is the size of the adjustment region 403 in the depth direction may be decided with consideration of the continuity of the retinal layer having a shape in which the boundaries of the retinal layer smoothly connect to themselves. For example, the range of 2d can be equal to or larger than 10 pixels and equal to or smaller than 30 pixels.

As described above, even when an upper portion of the tomographic image in which the retinal layer is folded back is present, the reverse-image generating section 113 can generate, using the tomographic image 401 and the reverse image 402, a new tomographic image. Note that the reverse image 402 is an image obtained by reversing the tomographic image 401 so that the reversed tomographic image 401 will be located on the side on which the retinal layer in the tomographic image 401 is in contact with an edge of the tomographic image 401. Furthermore, the above-mentioned side on which the retinal layer in the tomographic image 401 is in contact with an edge of the tomographic image 401 is the coherence-gate side in the tomographic image 401. For example, in the case where the coherence gate is moved to the choroid side of the eye to be examined and a tomographic image is obtained, the reverse image 402 can be an image obtained by reversing the tomographic image 401 so that the reversed tomographic image 401 will be located on the bottom side of the tomographic image 401.

Step S253

Figure 5A:
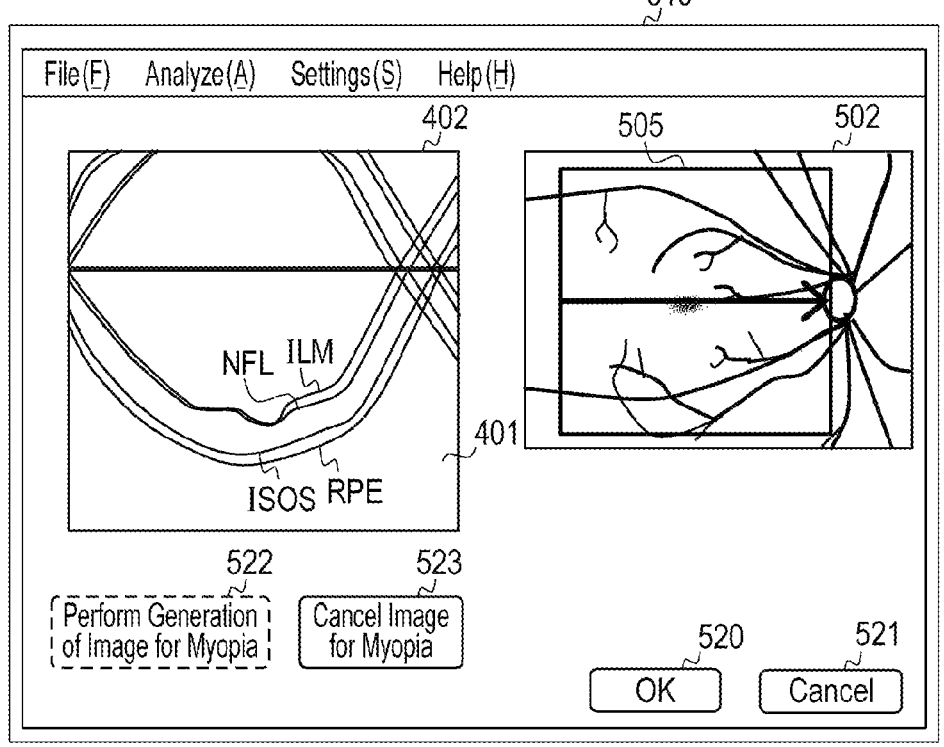
FIGS. 5A and 5B illustrate examples of display of results of image capture in the display screen of the display section of the image processing system according to the first embodiment.

In step S253, the tomographic image 401 and the reverse image 402, which have been generated in step S252, are displayed as image-capture-result check images as illustrated in FIG. 5A. Here, an image-capture-result check screen 510 illustrated in FIG. 5A includes the following: the tomographic image 401; the reverse image 402; an eye-fundus image 502; a mark 505 that indicates the image capture region in the case of image capture; a button 520 that is used to approve a result of image capture; a button 521 that is used to cancel a result of image capture; a button 522 that is used to provide an instruction to generate an image for myopia; and a button 523 that is used to cancel generation of an image for myopia. Note that, in FIG. 5A, because the image-capture-result check screen 510 is a screen in the case where image capture has been performed under the assumption that an image for myopia is to be generated, the button 522 used to provide an instruction to generate an image for myopia is in a state of being unselectable. The button 523 used to cancel generation of an image for myopia is in a state of being selectable.

Regarding display of the tomographic image 401 and the reverse image 402 illustrated in FIG. 5A, an example in which the tomographic image 401 is shifted in the downward direction by only the size of the reverse image 402 that has been added is illustrated. However, in the case where a limitation is imposed on a region in which a tomographic image is to be displayed, the tomographic image 401 can be displayed using an aspect ratio that is the same as the aspect ratio of an image which is used in the case of display of only the tomographic image 401, and the reverse image 402 can be displayed in accordance with the aspect ratio. The reason for this is that, in the case where the size of an image in the depth direction increases, when only the size of the image in the depth direction is reduced and displayed so that a tomographic image fits in a decided display region, the image in which the shape of the retinal layer is reduced in the depth direction is presented, and this leads to misunderstanding.

Step S254

In step S254, whether or not a normal image is to be generated or displayed is determined. More specifically, in the case where a specification for generating the tomographic image 401 and the reverse image 402 as an image for myopia has been provided in advance, when the button 523 used to cancel generation of an image for myopia is selected, display of the reverse image 402 is cancelled, and only the tomographic image 401 is displayed. This will be described in step S255 that is the next step. Note that, when the buttons 520 and 521 are selected without selecting the button 523 used to cancel generation of an image for myopia, the process proceeds to step S206.

Step S255

Figure 5B:
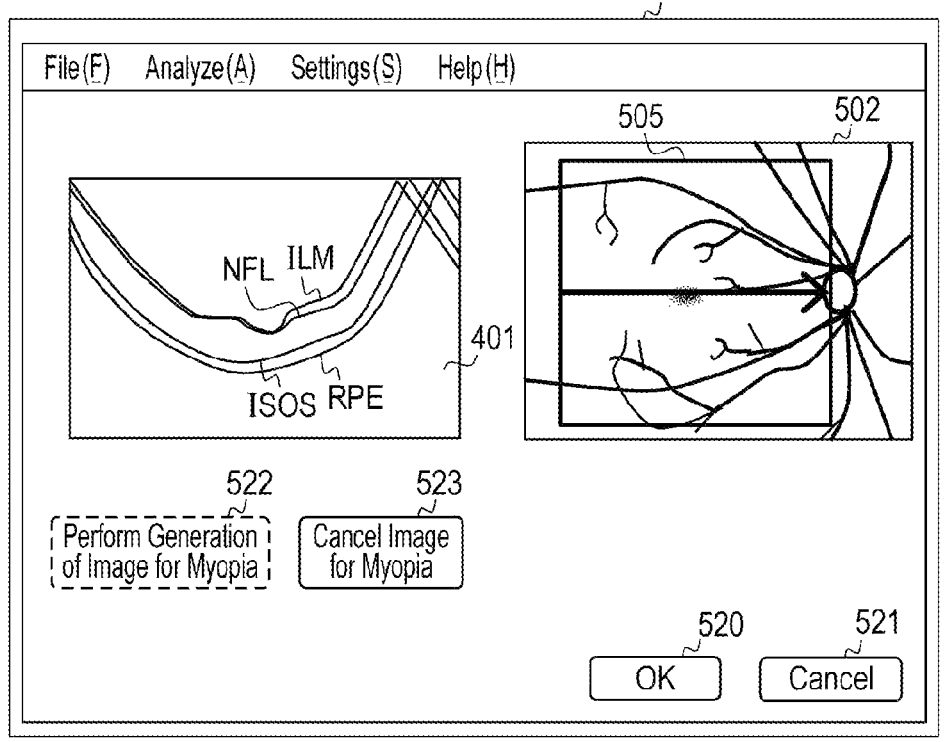

In step S255, a process for a case where a specification for generating an image for myopia has not been provided is performed. In the present embodiment, supposing that this process is performed in a case where image capture has been performed in an image capture mode other than the image capture mode for a highly myopic eye, the process will be described. In step S255, the tomographic image captured in step S204 is displayed. This will be described using FIG. 5B. An image-capture-result check screen 511 illustrated in FIG. 5B includes the following: the tomographic image 401; the eye-fundus image 502; a mark 505 that indicates the image capture region in the case of image capture; a button 520 that is used to approve a result of image capture; a button 521 that is used to cancel a result of image capture; a button 522 that is used to provide an instruction to generate an image for myopia; and a button 523 that is used to cancel generation of an image for myopia. Note that, in FIG. 5B, because the image-capture-result check screen 511 is a screen in the case where an image for myopia is not to be generated, the button 523 used to cancel generation of an image for myopia is in a state of being unselectable. The button 522 used to provide an instruction to generate an image for myopia is in a state of being selectable.

Step S256

In step S256, whether or not an instruction to generate a reverse image has been provided is determined. Here, the case where an instruction to generate a reverse image is provided is, for example, a case where although image capture has been performed in an image capture mode other than the image capture mode for a highly myopic eye, when a captured tomographic image is checked in the image-capture-result check screen, the retinal layer is folded back at the upper end of the tomographic image. In order to correct this, for example, the button 522 used to provide an instruction to generate an image for myopia is prepared in the image-capture-result check screen 511 so that a specification for generating the reverse image 402 will be provided. The button 522 is selected, whereby the specification section 116 provides, for the reverse-image generating section 113, a specification for generating a reverse image. In other words, the process proceeds to step S252 described above. Note that, when the buttons 520 and 521 are selected without selecting the button 522 used to provide an instruction to generate an image for myopia, the process proceeds to step S206.

Step S206

In step S206, an instruction acquisition section that is not illustrated acquires, from the outside, an instruction on whether or not image capture of a tomographic image with the image processing system 100 will be finished. This instruction is input using the operation section 600 by the operator. When the instruction acquisition section acquires an instruction to finish the process, the image processing system 100 finishes the process. In contrast, in the case of continuing image capture without finishing the process, the process returns to step S202, and image capture continues.

In this manner, the process of the image processing system 100 is performed.

With the above-described configuration, even when a tomographic image of the retinal layer that is highly curved, such as the retinal layer of a highly myopic eye, has been captured, the tomographic image can be displayed so that the shape of the entire retinal layer can be grasped.

Second Embodiment

Determine Whether or not Retinal Layer is in Contact with End of Tomographic Image In the foregoing first embodiment, an example is described, in which, even when a tomographic image of the retinal layer that is highly curved, such as the retinal layer of a highly myopic eye has been captured, a reverse image is generated and displayed for each tomographic image so that the shape of the entire retinal layer can be grasped. In a present embodiment, a determination section is newly provided, and whether or not the retinal layer is in contact with an end of a tomographic image is determined. Accordingly, whether or not a reverse image is to be generated can be automatically determined. Furthermore, whether or not a reverse image is to be displayed on the display section can also be automatically determined.

Figure 6:
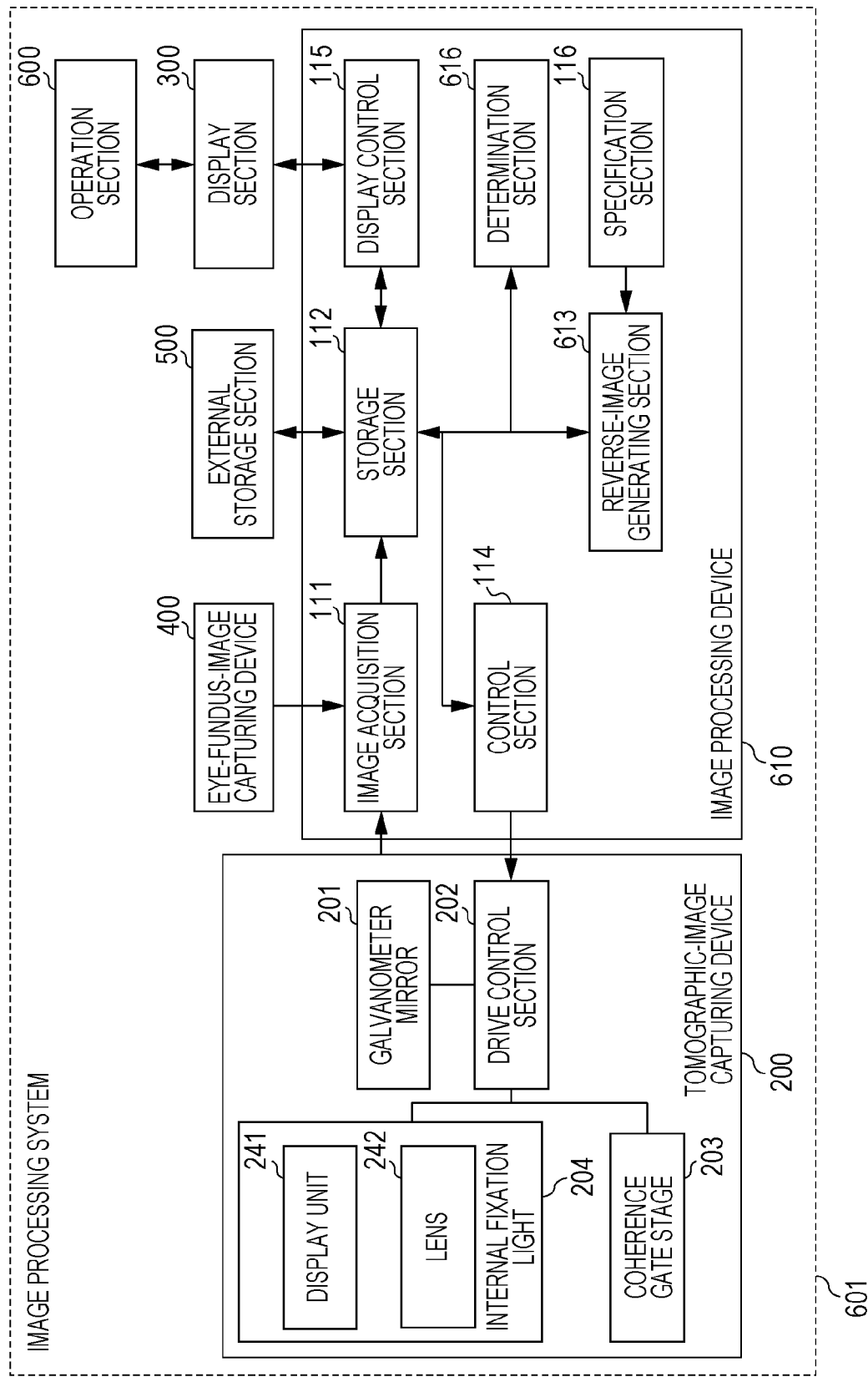
FIG. 6 is a diagram illustrating a configuration of an image processing system according to a second embodiment.

Hereinafter, the second embodiment will be described using FIGS. 6 and 7A to 7D. Note that, regarding elements having functions similar to the functions of the elements in the foregoing first embodiment, a description thereof is omitted. FIG. 6 is a diagram illustrating a configuration of an image processing system 601 including an image processing device 610 according to the present embodiment. In the present embodiment, a determination section 616 is the difference from the first embodiment. In the flow of a process, in step S251 illustrated in FIG. 2B, the determination method used to determine whether to generate a reverse image in the second embodiment is different from that in the first embodiment. In the first embodiment, image capture is performed in the image capture mode for a highly myopic eye, whereby whether to generate a reverse image is determined. Then, an example in which a reverse image is generated for each tomographic image that has been captured is described. In the present embodiment, the determination section 616 determines whether or not a reverse image needs to be generated for each tomographic image that has been captured. First, a case where a reverse image can be generated will be described using FIGS. 7A to 7D.

FIG. 7A illustrates an example of a tomographic image 701 in the case where the retinal layer is folded back in a tomographic image and a reverse image 702 of the tomographic image 701. FIG. 7B illustrates an example of the tomographic image 701 in the case where the retinal layer is folded back in a tomographic image and a reverse image 712 in the case where only a portion of the tomographic image in which a folded-back portion is present is reflected in a reverse image. As illustrated in FIG. 7B, only a portion of the tomographic image corresponding to a folded-back portion may be reflected in a reverse image, and, regarding the remaining portion of the tomographic image, an image generated using a pixel value, such as an interpolation image 705 illustrated in FIG. 7D, may be used. Accordingly, unnecessary information can be reduced. FIG. 7C illustrates an example of a tomographic image 703 in the case where no folded-back portion is present in a tomographic image and a reverse image 704 of the tomographic image 703. As illustrated in FIG. 7C, generation of a reverse image for a tomographic image for which it is not necessary to generate a reverse image is useless. When a plurality of tomographic images are captured by performing one scan, such as a three-dimensional raster scan or a radial scan, a case where reverse images need to be generated for some of the tomographic images and where reverse images not necessarily need to be generated for the remaining tomographic image will be described. In this case, regarding the tomographic images for which reverse images not necessarily need to be generated, an average value of pixel values of the background region from which the retinal layer is excluded is obtained, and is used as a pixel value of regions corresponding to reverse images. Alternatively, a value (for example, 0) that is decided in advance is used as the pixel value of regions corresponding to reverse images. This example is illustrated in FIG. 7D. FIG. 7D illustrates the tomographic image 703 and the interpolation image 705. The interpolation image 705 illustrated in FIG. 7D is an image that is generated for each of the tomographic images for which reverse images not necessarily need to be generated in the case of performing a three-dimensional raster scan or the like. Thus, the interpolation image 705 is not generated in the case where reverse images need or do not need to be generated for all of a plurality of tomographic images that have been captured by performing one scan. In other words, in the case of performing one scan, the interpolation image 705 is an image that is necessary to make the sizes of tomographic images in the horizontal or depth direction the same. Using the interpolation image 705, an aspect ratio can be made the same as the aspect ratio of the different tomographic image for which the reverse image 702 has been generated. Moreover, the size of reverse images and an interpolation image, in the depth direction, to be generated by the reverse-image generating section 613 is automatically determined by the determination section 616. Next a method for determining, with the determination section 616, whether or not a reverse image is to be generated, a method for deciding, with the determination section 616, the size of the reverse image, and an example of generation of a reverse image and an interpolation image with the reverse-image generating section 613 will be described.

First, the determination section 616 performs, on a tomographic image, a smoothing process using a median filter in order to remove noise, thereby obtaining an image. Next, the determination section 616 performs, on the obtained image, a binarization process using a determination and analysis method, thereby obtaining a binarized image. Then, the determination section 616 performs a labeling process on the binarized image. A size of each set of binarized regions can be detected by the labeling process. The determination section 616 removes sets of regions having small sizes, and leaves only sets of regions having large sizes. The determination section 616 performs, on the regions, an opening process or a closing process using morphology conversion, thereby leaving only a retinal-layer region. Note that the smoothing process and the method for automatically determining the threshold for binarization which are mentioned above are not limited thereto, and other methods may be used if similar results can be obtained using the methods. Furthermore, these processes are processes for detecting only the retinal-layer region. Thus, the processes can be performed after the size of an image has been reduced, whereby the processes can be performed at a higher speed. Whether or not the retinal layer is folded back is determined by determining whether or not the retinal-layer region is in contact with the upper left or right end of the image. This will be described using FIGS. 8A and 8B.

Figure 8A:
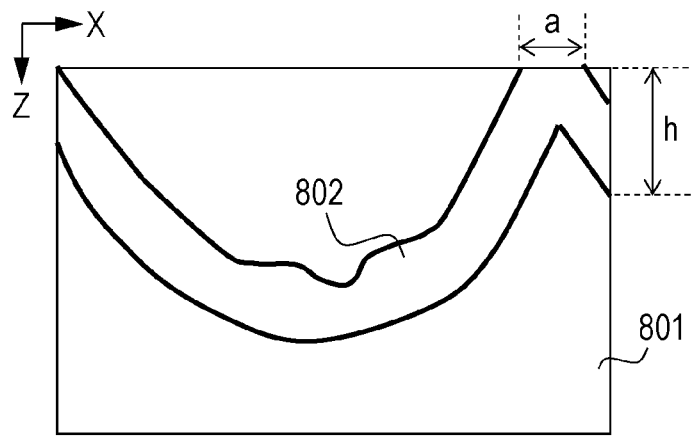
FIGS. 8A and 8B are diagrams for explaining generation of a reverse image which is performed in the image processing device according to the second embodiment.
Figure 8B:
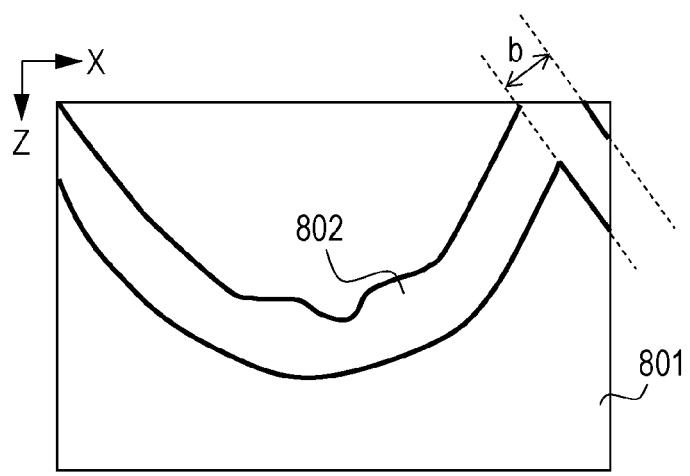

In FIGS. 8A and 8B, reference numeral 801 denotes a tomographic image, and reference numeral 802 denotes a retinal-layer region detected from the tomographic image. The example of generation of a reverse image illustrated in FIG. 7A will be described using FIG. 8A. Regarding the retinal-layer region 802, a size a is the size of the length of a portion of the retinal-layer region in which the retinal layer is in contact with the upper end of the tomographic image, and a size h is the size of the length of a portion of the retinal-layer region from the upper end of the tomographic image to the lower end of the retinal layer that is in contact with the right or left end of the tomographic image. When each of the size a and the size h is equal to or larger than a certain size, it is determined that the retinal layer is folded back at the upper end of the tomographic image. Here, each of the sizes a and h represents a value of a certain ratio with respect to the size of the tomographic image in a corresponding one of the vertical direction and the horizontal direction. For example, each of the sizes a and h is a size corresponding to a ratio of several percent. When each of the size a of the retinal-layer region 802 in which the retinal layer is in contact with the upper end of the tomographic image and the size h of the retinal-layer region in which the retinal layer is in contact with the left end or right end of the tomographic image is equal to or smaller than a certain size, no reverse image is generated. Note that, in the above description, the size a is the size of a length from the left end to the right end of the retinal layer at the right upper end of the tomographic image in the case of FIG. 8A. However, the size a is not limited thereto, and may be the size of a length from the left end of the retinal layer to the right end of the tomographic image. Furthermore, in the case of generation of a reverse image, the size of the reverse image in the depth direction may be decided in accordance with the size h. Next, an example in which only one portion of the tomographic image illustrated in FIG. 7B is reflected in a reverse image will be described using FIG. 8B. Here, as illustrated in FIG. 8B, a region including a portion of the retina-layer-image region in which the retinal layer is in contact with the upper end and the right end or left end of the tomographic image is set as a region of interest (ROI). The size of the region is denoted by b. Only an image included in the ROI is reflected in a reverse image, whereby the reverse image 702 is generated.

Regarding the size of a reverse image, when a plurality of tomographic images are present as in the case of performing a three-dimensional raster scan, processes similar to the above-described processes can be performed on all of the tomographic images, and then, the reverse-image generating section 613 can generate reverse images or an interpolation image in accordance with the largest of the sizes h of the retinal-layer regions of the tomographic images. Among the plurality of tomographic images, in the case where it is determined that reverse images need to be generated for some of the tomographic images, an interpolation image having a size the same as the size of the reverse images is generated for the remaining tomographic images. Note that an example is described, in which, among the plurality of tomographic images, in the case where it is determined that reverse images need to be generated for some of the tomographic images, an interpolation image is generated for all of the remaining tomographic images. However, generation of reverse images and an interpolation image is not limited thereto. For example, in the case where it is determined that a reverse image needs to be generated for only one tomographic image among 128 captured tomographic images, detection may be incorrectly performed. Thus, in the case where it is determined that reverse images need to be generated for the number of tomographic images that is a number equal to or larger than a threshold (for example, equal to or higher than thirty percent) among captured tomographic images, it may be determined that reverse images and an interpolation image are to be generated. Moreover, a method for automatically deciding the size of reverse images and an interpolation image in the depth direction is described. However, the size of reverse images and an interpolation image in the depth direction not necessarily need to be dynamically changeable. The sizes of reverse images and an interpolation image in the depth direction can be not necessarily different from each other on an image-capture-by-image-capture basis. Thus, the size of reverse images and an interpolation images in the depth direction may be a fixed value, or automatically selected from among several sizes (200 pixels, 300 pixels, 400 pixels, or and so forth) on the basis of the size h. As a matter of course, a configuration may be used, in which the size of reverse images in the depth direction of the retina is manually selected from a plurality of sizes such as the above-mentioned size.

Note that, in the present embodiment, an example is described, in which whether or not the retinal layer is folded back is automatically determined using the sizes a and h that are the size of the length of a portion of the retinal-layer region in which the retinal layer is in contact with the upper end of the tomographic image and the size of the length of a portion of the retinal-layer region in which the retinal layer is in contact with the right or left end of the tomographic image, respectively. However, a degree of contact of the retinal layer with the upper end of the tomographic image on each of the left and right sides (a portion corresponding to the size a illustrated in FIG. 8A) may be used as an indicator used to determine whether or not the retinal layer is folded back.

As described above, in the present embodiment, whether or not a reverse image is to be generated and the size of the reverse image can be automatically determined by the determination section. Accordingly, a reverse image can be generated only when a reverse image needs to be generated. Even when a tomographic image of the retinal layer that is highly curved, such as the retinal layer of a highly myopic eye, has been captured, the tomographic image can be displayed so that the shape of the entire retinal layer can be grasped.

Third Embodiment

Analyze Retinal Layer in Reverse Image

Figure 9:
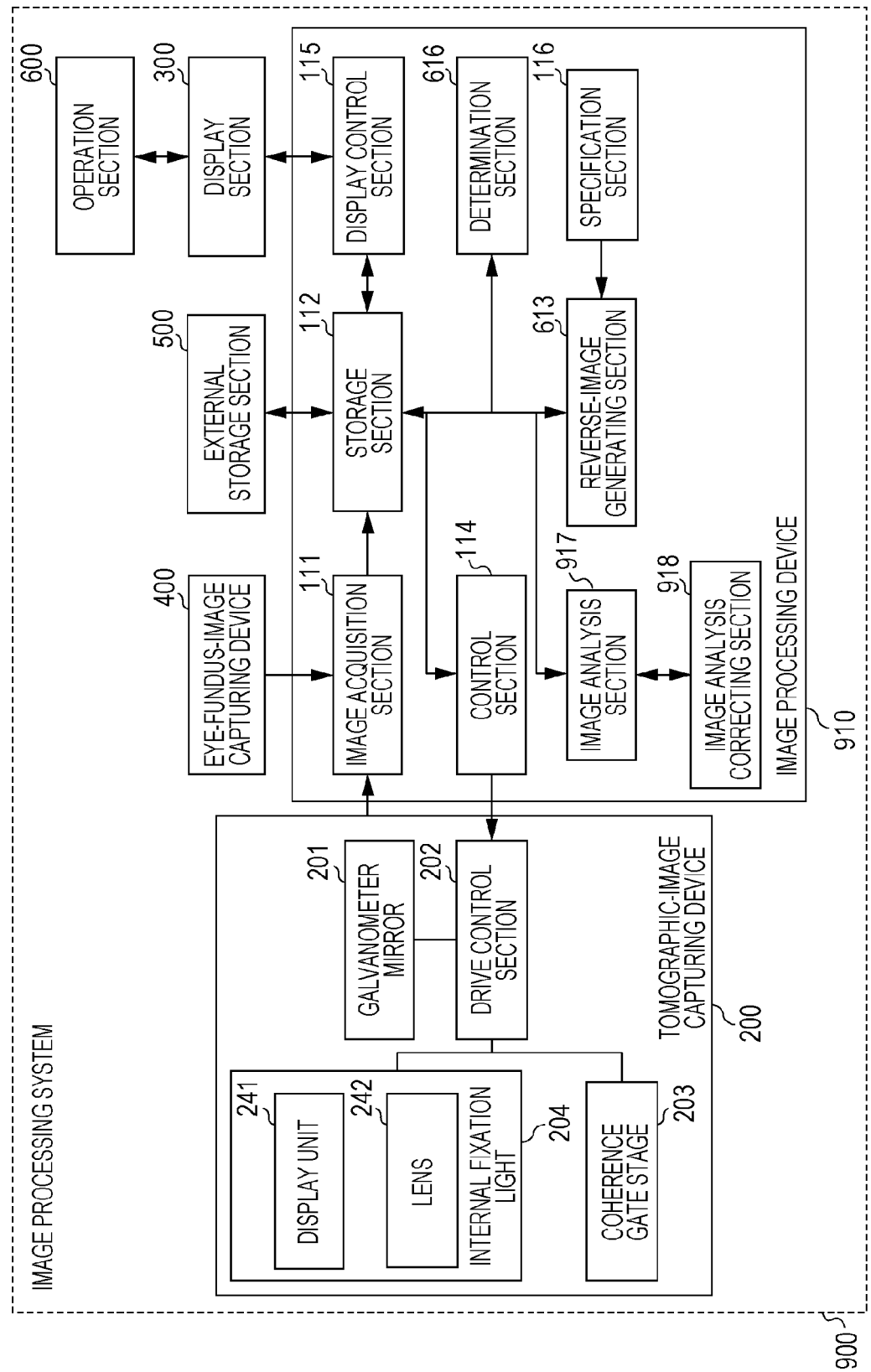
FIG. 9 is a diagram illustrating a configuration of an image processing system according to a third embodiment.

In the foregoing first and second embodiments, examples in which generation of a reverse image is performed in the case of checking a result of image capture is described. In a present embodiment, an example will be described, in which an image analysis section is further provided, and in which generation of a reverse image is performed in the case of image analysis. This will be described using FIGS. 9, and 10A and 10B. Note that, regarding elements having functions similar to the functions of the elements in the foregoing first and second embodiments, a description thereof is omitted. FIG. 9 is a diagram illustrating a configuration of an image processing system 900 including an image processing device 910 according to a present embodiment. In the present embodiment, an image analysis section 917 and an image analysis correcting section 918 are the differences from the first and second embodiments. The image analysis section 917 detects boundaries of the retinal layer from the retinal layer, and performs analysis of the thickness or shape of the retinal layer. In the flow of a process illustrated in FIGS. 10A and 10B, steps S1005 and S1006 are the differences.

In the present embodiment, an example will be described, in which an image analysis section is further provided, and in which generation of a reverse image is not performed in the case of checking a result of image capture but generation of a reverse image is performed in the case of image analysis.

Step S1005

In step S1005, a check image is displayed as a result of image capture. This will be described with reference to FIGS. 5A and 5B described in the first embodiment. In the first embodiment, whether or not a reverse image is to be generated is determined in the image-capture-result check screen. However, the present embodiment will be described supposing that determination of whether or not a reverse image is to be generated is not performed. Thus, a screen that may be displayed as the image-capture-result check screen 511 illustrated in FIG. 5B includes the following: the tomographic image 401; the eye-fundus image 502; the mark 505 indicating the image capture region in the case of image capture; the button 520 used to approve a result of image capture; and the button 521 used to cancel a result of image capture. In other words, in the present embodiment, the button 522 used to provide an instruction to generate an image for myopia and the button 523 used to cancel generation of an image for myopia do not need to be displayed. Accordingly, in the case of quickly performing image capture and of performing analysis later, the operator can focus on only image capture.

Step S1006

In step S1006, the display control section 115 performs analysis of a tomographic image, and displays a result of analysis on the display section 300. This process will be described with reference to FIGS. 10B and 11A to 11C.

Step S1061

Figure 11A:
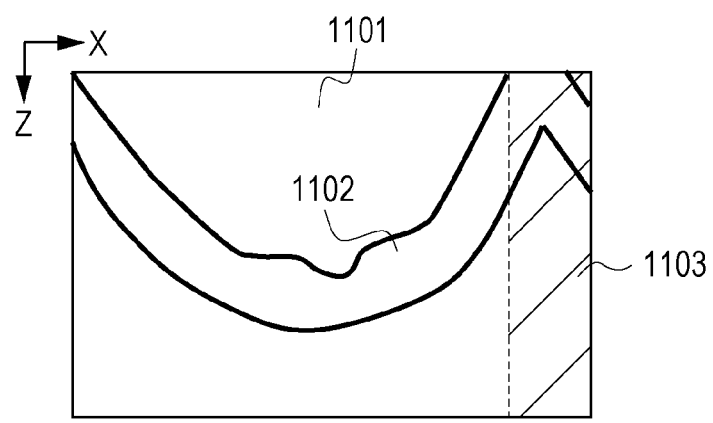
FIGS. 11A to 11C are diagrams for explaining image analysis which is performed in the image processing device according to the third embodiment.
Figure 11B:
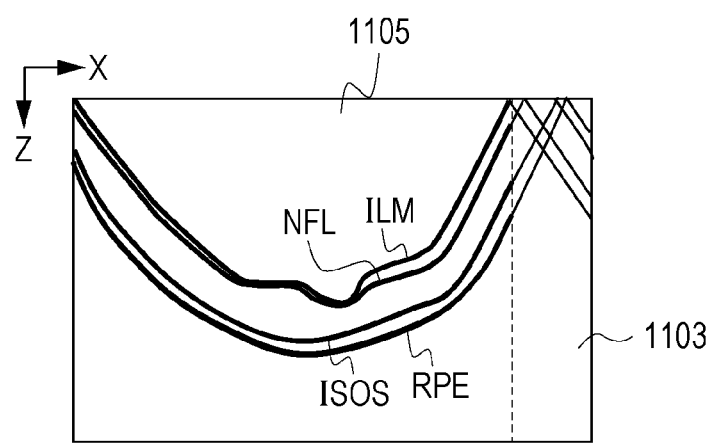

In step S1061, the image analysis section 917 performs detection of the retinal layer. This will be described using FIGS. 11A to 11C. In FIG. 11A, a retinal-layer region 1102 detected by the determination section 616 is illustrated. The determination section 616 performs this process using the method described in the second embodiment. A mask region 1103 (a region filled with diagonal lines at the right side of FIG. 11A) is set in a portion in which a region in which the retinal layer is in contact with the upper end and the left or right end of a tomographic image exists. Detection of the retinal layer in the portion is not performed. The image analysis section 917 performs detection of the retinal layer from the tomographic image from which the portion in which the mask region is set is excluded. The image analysis section 917 detects any one of individual boundaries that are the boundaries of the inner limiting membrane (ILM), the boundary between the nerve fiber layer (NFL) and the ganglion cell layer (GCL), the boundaries of the photoreceptor inner/outer segment junction (ISOS), and the boundaries of the retinal pigment epithelium (RPE). First, the image analysis section 917 applies individually a median filter and a Sobel filter to the tomographic image 1105, thereby generating images (hereinafter, referred to as a "median image" and a "Sobel image"). Next, the image analysis section 917 generates profiles from the median image and the Sobel image, which have been generated, on an A-scan-by-A-scan basis. A profile based on brightness values is generated from the median image, and a profile based on gradients is generated from the Sobel image. The image analysis section 917 detects peaks in the profile generated from the Sobel image. The image analysis section 917 detects the boundaries between individual regions of the retinal layer with reference to contents that are contents of the profile generated from the median image and that correspond to values before and after the detected peaks or between the peaks. Here, examples of detected boundaries of the retinal layer are illustrated in FIG. 11B. The detected boundary lines are illustrated with the thick lines in FIG. 11B. As illustrated in FIG. 11B, regarding the mask region 1103 in which the retinal layer is folded back at the upper end of the tomographic image, because it is difficult to detect the retinal layer in the mask region 1103, detection of the retinal layer in the mask region 1103 is not performed.

Step S1062

In step S1062, whether or not a specification for generating a reverse image has been provided in the case of image capture is determined. In the present embodiment, whether or not a reverse image or an interpolation image is to be generated is determined by the determination section 616 as in the second embodiment. When it is determined that reverse images and an interpolation image need to be generated for some of a plurality of tomographic images captured by performing one scan, the process proceeds to step S1063. Note that, it is determined that reverse images and an interpolation image do not need to be generated, the process proceeds to step S1068. This will be described below.

Step S1063

In step S1063, the reverse-image generating section 613 performs generation of a reverse image. Regarding generation of a reverse image, as described in the second embodiment, the size of reverse images and an interpolation image to be generated by the reverse-image generating section 613 is decided by a result of determination performed by the determination section 616.

Step S1064

Figure 11C:
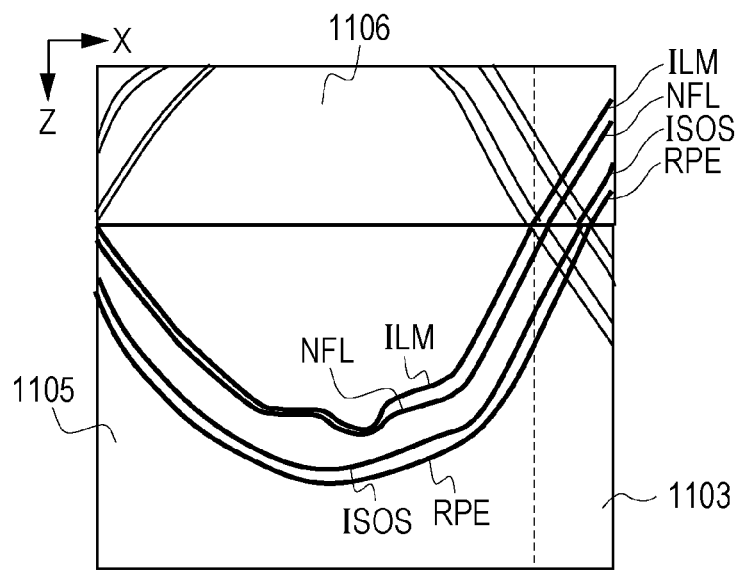

In step S1064, a detection unit of the image analysis section 917 performs detection of the retinal layer in a reverse-image region. The image analysis section 917 detects the retinal layer in the reverse-image region with respect to the boundaries of the retinal layer which have been detected in step S1061. Using the positions of boundary lines adjacent to the mask region 1103 illustrated in FIG. 11B as initial values, an edge is searched for in the mask region and the reverse-image region. In this case, an edge is searched for in a direction in which the boundary lines are continuously present, and, in FIGS. 11A to 11C, an edge that is continuous in the upper-right direction is searched for. The Sobel filter is set so as to detect an edge extending in an oblique direction so that the boundaries of the retinal layer will be easily detected in these regions. Note that, in the case where regions in which the retinal layer is folded back are present at both the left end and the right end, different filters can be applied to the left end and the right end so that edges in individual directions will be easily detected. Here, examples of the detected boundaries of the retinal layer are illustrated in FIG. 11C. In FIG. 11C, the detected boundary lines are illustrated with the thick lines. As illustrated in FIG. 11C, the boundaries of the retinal layer are detected in the mask region 1103 in which the retinal layer is folded back at the upper end of the tomographic image and also in the reverse-image region 1106. As described above, the boundaries of the retinal layer can be detected with consideration of the continuity of the retinal layer having a shape in which the boundaries of the retinal layer smoothly connect to themselves.

Step S1065

In step S1065, the image analysis section 917 performs shape analysis. As shape analysis, for example, the image analysis section 917 calculates the thickness or curvature of the retinal layer. Regarding the thickness of the retinal layer, for example, it is supposed that the ILM and the RPE are detected. In this case, the image analysis section 917 calculates the thickness of the entire retinal layer. In FIGS. 11A to 11C, the thickness of the retinal layer can be calculated by obtaining the difference between the z coordinate of the ILM and the z coordinate of the RPE at each x coordinate in the XZ plane. Additionally, not only the thickness of the retinal layer, but also the area or volume of the retinal layer may be obtained. The area of the retinal layer can be calculated by adding the thicknesses of layers at individual coordinates along the X axis in one tomographic image. The volume of the retinal layer can be calculated by adding obtained areas along the Y-axis direction. These results of calculation are stored in the storage section 112. Here, an example of calculation of the entire retinal layer is described. However, the area or volume of another layer (for example, the NFL) can be similarly obtained.

Furthermore, in the case of calculating the curvature of the retinal layer, the curvature of the boundary line of a layer (the RPE) that is a target for shape analysis is calculated. A curvature k can be obtained by calculating Equation (1) for each point of the boundary line. Whether the layer projects in the upward direction or the downward direction can be determined on the basis of the sign of the curvature k, and the degree of curvature of the shape is determined on the basis of the size of the number of the curvature k. Thus, in the case where projection in the upward direction is represented by + and where projection in the downward direction is represented by −, when a region having a curvature whose sign is −, a region having a curvature whose sign is +, and a region having a curvature whose sign is − are present in individual tomographic images, this represents a W shape. The sign of the curvature of a layer changes in accordance with whether the layer projects in the upward direction or the downward direction. Thus, a desired result can be obtained by performing analysis using a shape close to the original shape of the retinal layer without using a shape of the retinal layer in a state in which the retinal layer is folded back at the upper end of a tomographic image.

$$k = \frac{\frac{d^2z}{dx^2}}{\left(1+\left(\frac{dz}{dx}\right)\right)^{\frac{3}{2}}} \quad (1)$$

Note that, here, a case where a curvature is calculated using boundaries lines in a tomographic image is described. However, calculation of a curvature is not limited thereto. A three-dimensional curvature may be calculated from three-dimensional data.

Note that, when the boundaries of the retinal layer have been incorrectly detected by the image analysis section 917, the image analysis correcting section 918 can make a modification manually in accordance with an instruction provided by the operator.

Step S1066

Figure 12A:
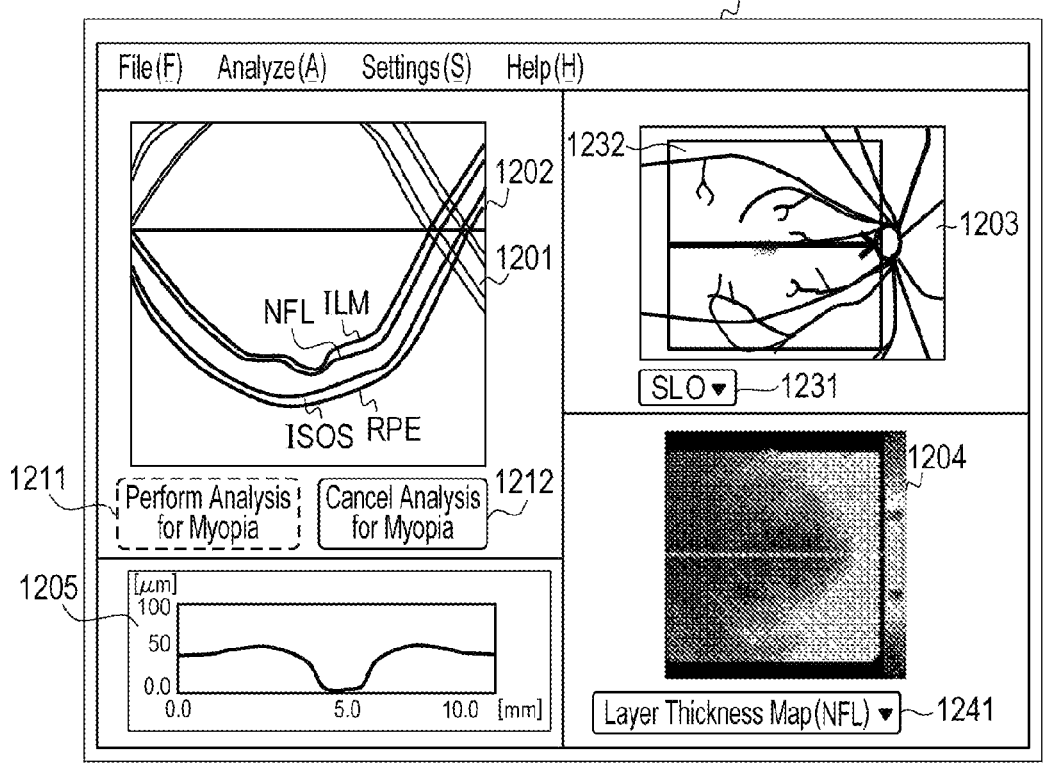
FIGS. 12A and 12B illustrate examples of display of results of analysis in a display screen of a display section of the image processing system according to the third embodiment.
Figure 12B:
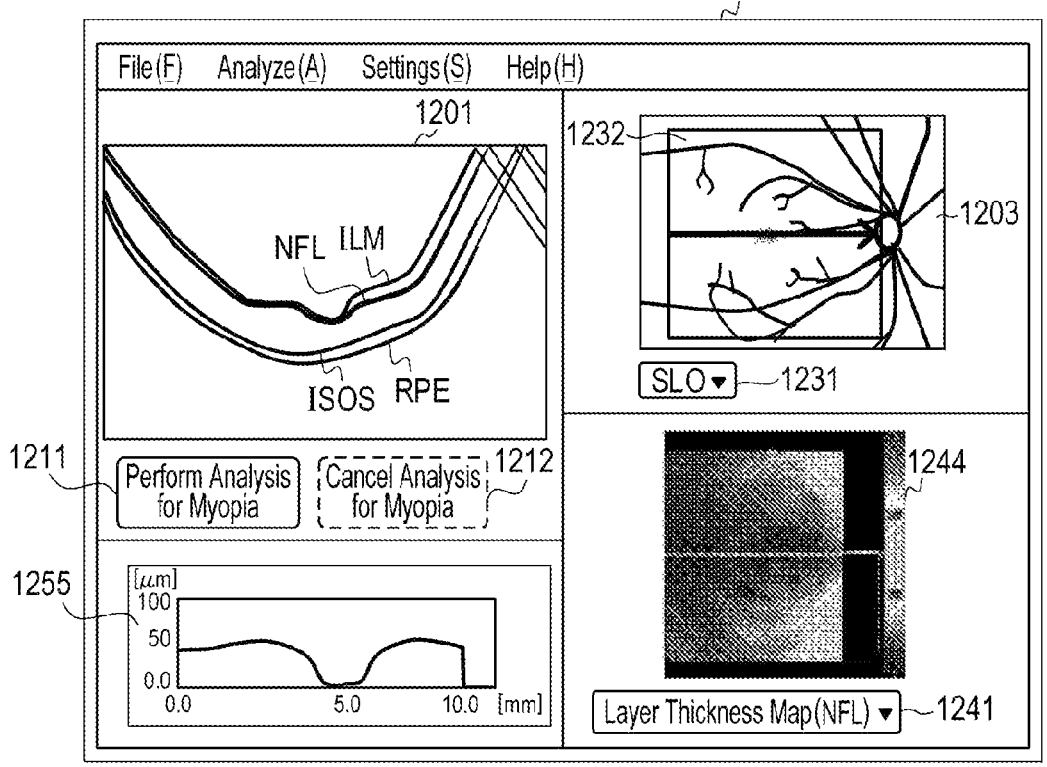

In step S1066, a check image is displayed as a result of analysis. This example is illustrated in FIGS. 12A and 12B. In FIG. 12A, reference numeral 1210 denotes a tomographic-image observation screen. Reference numeral 1201 denotes a tomographic image. Reference numeral 1202 denotes a reverse image. Reference numeral 1211 denotes a myopia-analysis execution button. Reference numeral 1212 denotes a myopia-analysis cancel button. In step S1066, because step S1066 is included in the flow in which a reverse image has been generated, the myopia-analysis execution button 1211 is in a state of being unselectable. The myopia-analysis cancel button 1212 is in a state of being selectable. A result of detection of the boundaries of the retinal layer is superimposed and displayed on the tomographic image 1201 and the reverse image 1202. Note that, in the case where the size of a region in which a tomographic image is to be displayed is decided, without performing a process of reducing the size of an image only in the depth direction, the tomographic image 1201 can be displayed using an aspect ratio that is the same as the aspect ratio of an image which is used in the case of display of only the tomographic image 1201, and the reverse image 1202 can be displayed in accordance with the aspect ratio.

Reference numeral 1203 denotes SLO (an eye-fundus image). Reference numeral 1232 denotes the image capture range that is superimposed and displayed on an image using the SLO. Reference numeral 1231 denotes an eye-fundus-image switching combo box. Regarding an eye-fundus photograph, an eye-fundus photograph+SLO, SLO+an analysis map, and so forth, switching among them can be performed by switching the eye-fundus-image switching combo box, and, consequently, any one of them can be displayed.

Reference numeral 1204 denotes a layer-thickness map. Reference numeral 1241 denotes a map-type switching combo box. Reference numeral 1205 denotes a layer-thickness graph. Regarding the types of maps such as an entire-retinal-layer-thickness map and a curvature map, switching among the types of maps is performed by switching the map-type switching combo box 1241, and, consequently, any one of the types of maps can be displayed. Regarding the layer-thickness graph 1205, the type of graph to be displayed can also be switched in accordance with the type of map.

As shown in the examples illustrated in FIGS. 12A and 12B, even when a region in which the retinal layer is folded back at the upper end of the tomographic image is present, the retinal-layer region in the entire image can be detected. Thus, the layer-thickness map 1204 and the layer-thickness graph 1205 do not have any defective portion, and a state in which analysis of the entirety has been performed can be displayed.

Step S1067

In step S1067, the myopia-analysis cancel button 1212 is selected, whereby the process proceeds to step S1069. When the myopia-analysis cancel button 1212 is not selected, the process returns from the image analysis/display process to the main flow.

Step S1068

In step S1068, in the case where no reverse image is generated, the image analysis section 917 performs shape analysis. As a method for shape analysis, a method similar to the method used in step S1065 is used. However, shape analysis is performed on a region the tomographic image 1105 from which the mask region 1103 illustrated in FIG. 11B is excluded.

Step S1069

In step S1069, a check image is displayed as a result of analysis. This will be described using FIG. 12B. A screen configuration similar to that illustrated in FIG. 12A is illustrated in FIG. 12B. However, in FIG. 12B, a tomographic image 1201 is displayed, but a reverse image 1202 is not displayed. Furthermore, a display form indicating the boundaries of the retinal layer is superimposed and displayed on the tomographic image. However, a range in which the retinal layer has been detected extends only to a region in which the retinal layer is not in contact with the upper end of the tomographic image. Furthermore, the myopia-analysis execution button 1211 is in a state of being selectable, and the myopia-analysis cancel button 1212 is in a state of being unselectable.

As illustrated in FIG. 12B, in the tomographic image 1201, in the case where a region in which the retinal layer is folded back is present, a layer-thickness map 1244 and a layer-thickness graph 1255 have defective regions.

Step S1070

In step S1070, the myopia-analysis execution button 1211 is selected, whereby the process proceeds to step S1063. When the myopia-analysis execution button 1211 is not selected, the process returns from the image analysis/display process to the main flow.

Note that, in the present embodiment, an example is described, in which an image analysis section is provided, and in which generation of a reverse image is not performed in the case of checking a result of image capture but generation of a reverse image is performed in the case of image analysis. Generation of a reverse image is not necessarily limited thereto. For example, if whether to perform generation of a reverse image is checked in the case of checking a result of image capture, whether to perform generation of a reverse image does not need to be checked in the case of image analysis. In this case, in the flow of the process illustrated in FIGS. 10A and 10B, in step S1062, the flow of the process is divided on the basis of a result of determination performed in the case of checking a result of image capture. The flows of the determination processes performed in steps S1067 and S1070 become unnecessary.

As described above, in the present embodiment, detection of the retinal layer and analysis of the shape of the retinal layer can be performed by the image analysis section. Furthermore, in the case where a reverse image is to be generated and also in the case where a reverse image is not to be generated, analysis can be performed. Even when a tomographic image of the retinal layer that is highly curved, such as the retinal layer of a highly myopic eye, has been captured, the tomographic image can be displayed so that the shape of the entire retinal layer can be grasped, and a result of shape analysis can be displayed.

Fourth Embodiment

Display Result of Analysis of New Generated Tomographic Image

In the foregoing first to third embodiments, examples are described, in which, when a tomographic image of the retinal layer that is highly curved, such as the retinal layer of a highly myopic eye, has been captured, the shape of the entire retinal layer is displayed by generating a reverse image. In a present embodiment, an example will be described, in which a display form indicating a result of analysis is displayed without displaying the shape of the entire retinal layer. Note that, regarding elements having functions similar to the functions of the elements in the foregoing first to third embodiments, a description thereof is omitted.

Figure 13:
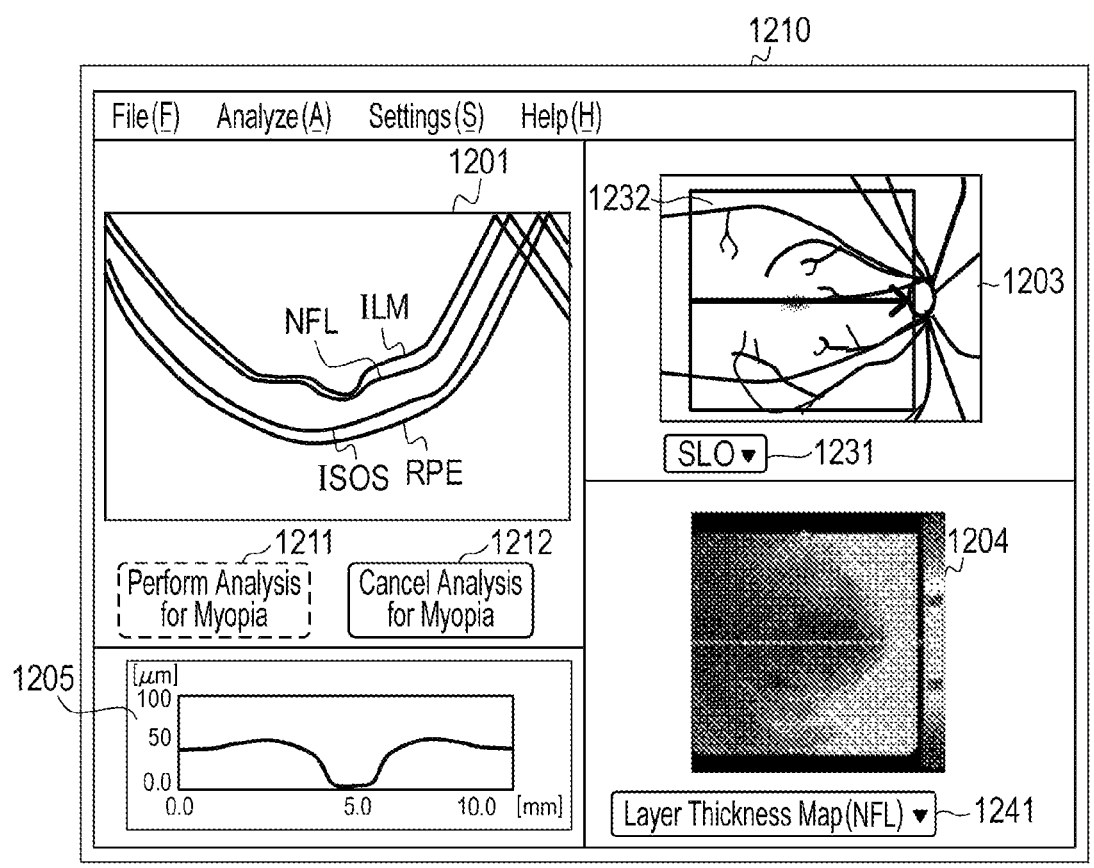
FIG. 13 illustrates an example of display of a result of analysis in a display screen of a display section of an image processing system according to a fourth embodiment.

The present embodiment will be described with reference to the flow illustrated in FIGS. 10A and 10B, which are used in the third embodiment, and FIG. 13. Referring to FIG. 10B, display of a check image in step S1066 will be described. As illustrated in FIG. 13, in the present embodiment, in step S1066, a reverse image is not displayed, and the tomographic image 1201 is displayed. In addition, a result of detection of the boundaries of the retinal layer is superimposed and displayed on the tomographic image 1201. In this case, a result of detection of the boundaries of the retinal layer that have been detected using the reverse image which is not displayed is reversed upside down, and superimposed and displayed on the tomographic image 1201. Accordingly, even when the reverse image is not displayed, the layer-thickness graph 1205 having a high accuracy can be displayed using the result of detection of the boundaries of the retinal layer that have been detected using the reverse image.

As described above, in the present embodiment, detection of the retinal layer and analysis of the shape of the retinal layer can be performed by the image analysis section. Furthermore, in the case where a reverse image is to be generated and also in the case where a reverse image is not to be generated, analysis can be performed. Even when a tomographic image of the retinal layer that is highly curved, such as the retinal layer of a highly myopic eye, has been captured, a result of shape analysis of the shape of the entire retinal layer can be displayed. Note that the layout of a user interface, such as a button, or the layout of a display form is not limited to the above-described layout.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-053599, filed Mar. 15, 2013, which is hereby incorporated by reference herein in its entirety.

What is claimed is:

1. An image processing device comprising:
an acquisition unit configured to acquire a tomographic image of a retina of an eye to be examined;
a generating unit configured to generate a new tomographic image, using the acquired tomographic image and a reverse image in which at least one portion of the acquired tomographic image is reversed, so that the reverse image is located on a side on which a retinal layer in the acquired tomographic image is in contact with an end of the acquired tomographic image; and
a detection unit configured to detect at least one retinal layer in the acquired tomographic image, and to detect, based on continuity between the detected at least one retinal layer in the acquired tomographic image and at least one retinal layer in the reverse image, the at least one retinal layer in the new generated tomographic image.

2. The image processing device according to claim 1, wherein the side on which the retinal layer in the acquired tomographic image is in contact with an end of the acquired tomographic image is a coherence-gate side in the acquired tomographic image.

3. The image processing device according to claim 1, further comprising
a display control unit configured to cause a display unit to display the new generated tomographic image.

4. The image processing device according to claim 3, further comprising
wherein the display control unit causes the display unit to display a display form indicating the detected at least one retinal later in the new generated tomographic image in a state in which the display form is superimposed on the new generated tomographic image.

5. The image processing device according to claim 3, further comprising
a determination unit configured to determine whether or not the retinal layer is in contact with an end of the acquired tomographic image,
wherein, when the retinal layer is in contact with an end of the tomographic image, the display control unit causes the display unit to display the new generated tomographic image.

6. The image processing device according to claim 3, further comprising
an instruction unit configured to provide an instruction to generate the reverse image,
wherein the display control unit causes, in accordance with the instruction provided by the instruction unit, the display unit to display the new generated tomographic image.

7. The image processing device according to claim 3, wherein, when the acquired tomographic image is captured in an image capture mode for a highly myopic eye, the display control unit causes the display unit to display the new generated tomographic image.

8. The image processing device according to claim 3, further comprising
a selection unit configured to cause the display unit to display any one of the new generated tomographic image and the reverse image.

9. The image processing device according to claim 1, further comprising:
an image analysis unit configured to analyze, using the detected at least one retinal layer in the new generated tomographic image, the new generated tomographic image; and
a display control unit configured to cause a display unit to display a display form indicating a result of analysis performed by the image analysis unit.

10. The image processing device according to claim 9, wherein the image analysis unit is configured to calculate a thickness of the detected at least one retinal layer in the new generated tomographic image, and
wherein the display control unit is configured to cause the display unit to display, as the display form, at least one of a map of the calculated thickness and a graph of the calculated thickness.

11. The image processing device according to claim 9, wherein the image analysis unit is configured to calculate a curvature of the detected at least one retinal layer in the new generated tomographic image, and
wherein the display control unit is configured to cause the display unit to display, as the display form, a map of the calculated curvature.

12. The image processing device according to claim 1, further comprising
a selection unit configured to select a range of a reverse image in a depth direction of the retina from among a plurality of ranges,
wherein the generating unit generates a reverse image having the selected range, and generates, using the generated reverse image and the acquired tomographic image, a new tomographic image.

13. An image processing system comprising:
the image processing device according to claim 1; and
an optical coherence tomography device configured to capture the acquired tomographic image,
wherein the image processing device and the optical coherence tomography device are connected to each other so as to be capable of communicating with each other.

14. The image processing device according to claim 1, wherein a noise region which is a part of the acquired tomographic image and is located on the side is removed.

15. An image processing device comprising:
an acquisition unit configured to acquire a tomographic image of a retina of an eye to be examined;
a detection unit configured to detect at least one retinal layer in the acquired tomographic image;
an image analysis unit configured to analyze the detected at least one retinal layer of a portion that is an overlap between the detected at least one retinal layer in the acquired tomographic image and a folded-back portion of the detected at least one retinal layer on a side on which the detected at least one retinal layer is in contact with an end of the acquired tomographic image; and
a display control unit configured to cause a display unit to display the tomographic image and a display form indicating a result of analysis performed by the image analysis unit.

16. The image processing device according to claim 15, wherein a direction in which the image analysis unit detects the retinal layer in the folded-back portion differs in accordance with a right end or left end of the acquired tomographic image.

17. An image processing system comprising:
the image processing device according to claim 15; and
an optical coherence tomography device configured to capture the acquired tomographic image,
wherein the image processing device and the optical coherence tomography device are connected to each other so as to be capable of communicating with each other.

18. The image processing device according to claim 15,
wherein the image analysis unit is configured to calculate a thickness of the detected at least one retinal layer, and
wherein the display control unit is configured to cause the display unit to display, as the display form, at least one of a map of the calculated thickness and a graph of the calculated thickness.

19. The image processing device according to claim 15,
wherein the image analysis unit is configured to calculate a curvature of the detected at least one retinal layer, and
wherein the display control unit is configured to cause the display unit to display, as the display form, a map of the calculated curvature.

20. An image processing method comprising:
a step of acquiring a tomographic image of a retina of an eye to be examined; and
a step of generating a new tomographic image, using a reverse image in which at least one portion of the acquired tomographic image is reversed and the acquired tomographic image, so that the reverse image is located on a side on which a retinal layer in the acquired tomographic image is in contact with an end of the acquired tomographic image;
a step of detecting at least one retinal later in the acquired tomographic image; and
a step of detecting, based on continuity between the detected at least one retinal later in the acquired tomographic image and at least one retinal layer in the reverse image, the at least one retinal layer in the new generated tomographic image.

21. A non-transitory computer-readable storage medium storing a program causing a computer to execute the steps of the image processing method according to claim 20.

22. An image processing method comprising:
a step of acquiring a tomographic image of a retina of an eye to be examined;
a step of detecting at least one retinal later in the acquired tomographic image;
a step of analyzing the detected at least one retinal layer of a portion that is an overlap between the retinal layer in the acquired tomographic image and a folded-back portion of the detected at least one retinal layer on a side on which the detected at least one retinal layer is in contact with an end of the acquired tomographic image; and
a step of causing a display unit to display the tomographic image and a result of analysis in the analysis step.

23. A non-transitory computer-readable storage medium storing a program causing a computer to execute the steps the image processing method according to claim 22.

24. An image processing device comprising:
an acquisition unit configured to acquire a tomographic image of a retina of an eye to be examined; and
a detection unit configured to detect at least one retinal layer in the acquired tomographic image, and to detect, based on continuity between the detected at least one retinal layer in the acquired tomographic image and at least one retinal layer in a reverse image of at least one portion of the acquired tomographic image, the at least one retinal layer in the reverse image.

25. The image processing device according to claim 24, further comprising:
an image analysis unit configured to analyze, using the detected at least one retinal layer in the acquired tomographic image and the reverse image, the acquired tomographic image and the reverse image; and
a display control unit configured to cause a display unit to display a display form indicating a result of analysis performed by the image analysis unit.

26. The image processing device according to claim 25,
wherein the image analysis unit is configured to calculate a thickness of the detected at least one retinal layer in the acquired tomographic image and the reverse image, and
wherein the display control unit is configured to cause the display unit to display, as the display form, at least one of a map of the calculated thickness and a graph of the calculated thickness.

27. The image processing device according to claim 25,
wherein the image analysis unit is configured to calculate a curvature of the detected at least one retinal layer in the acquired tomographic image and the reverse image, and
wherein the display control unit is configured to cause the display unit to display, as the display form, a map of the calculated curvature.

28. An image processing method comprising:
a step of acquiring a tomographic image of a retina of an eye to be examined;
a step of detecting at least one retinal layer in the acquired tomographic image; and
a step of detecting, based on continuity between the detected at least one retinal layer in the acquired tomographic image and at least one retinal layer in a reverse image of at least one portion of the acquired tomographic image, the at least one retinal layer in the reverse image.

29. A non-transitory computer-readable storage medium storing a program causing a computer to execute the steps of the image processing method according to claim 28.

* * * * *